(12) United States Patent
Shimada et al.

(10) Patent No.: US 7,897,562 B2
(45) Date of Patent: Mar. 1, 2011

(54) APOPTOSIS-INDUCING AGENT AND METHOD FOR INDUCING APOPTOSIS

(75) Inventors: Hideaki Shimada, Chiba (JP); Kazuyuki Matsushita, Chiba (JP); Takeshi Tomonaga, Chiba (JP); Fumio Nomura, Chiba (JP); Takenori Ochiai, Chiba (JP)

(73) Assignee: National University Corporation Chiba University, Chiba (JP)

( * ) Notice: Subject to any disclaimer, the term of this patent is extended or adjusted under 35 U.S.C. 154(b) by 238 days.

(21) Appl. No.: 12/010,533

(22) Filed: Jan. 25, 2008

(65) Prior Publication Data

US 2008/0227705 A1 Sep. 18, 2008

Related U.S. Application Data

(62) Division of application No. 10/554,026, filed as application No. PCT/JP2004/004516 on Mar. 30, 2004, now abandoned.

(30) Foreign Application Priority Data

Apr. 21, 2003 (JP) .............................. 2003-116299

(51) Int. Cl.
*C07K 14/00* (2006.01)
(52) U.S. Cl. .......................................... 514/2; 530/350
(58) Field of Classification Search ....................... None
See application file for complete search history.

(56) References Cited

FOREIGN PATENT DOCUMENTS

WO 01/96873 A2 12/2001

OTHER PUBLICATIONS

Liu et al. 2000; The FBP interacting repressor targets TFIIH to inhibit activated transcription. Molecular Cell 5: 331-341.*

Bouffard et al. 2000; Interaction cloning and characterization of RoBPI, a novel protein binding to human Ro ribonucleoproteins. RNA 6: 66-78.*

Thompson, E. B., "The Many Roles of c-Myc in Apoptosis," Annual Review of Physiology, 1998, vol. 60, pp. 575-600.

Pelengaris et al.; "Suppression of Myc-Induced Apoptosis in Beta Cells Exposes Multiple Oncogenic Properties of Myc and Triggers Carcinogenic Progression" Cell, May 3, 2002, vol. 109, pp. 321-334.

Thiede et al.; "Predominant Identification of RNA-binding Proteins in FAS-induced Apoptosis by Proteome Analysis", Journal of Biological Chemistry, Jul. 13, 2001, vol. 276, No. 28, pp. 26044-26050.

Brockstedt et al.; "Identification of Apoptosis-associated Proteins in a Human Burkitt Lymphoma Cell Line", Journal of Biological Chemistry, Oct. 23, 1998, vol. 273, No. 43, pp. 28057-28064.

Supplementary European Search Report dated Jun. 15, 2009 for EP Appln. No. 04 72 4383.

* cited by examiner

*Primary Examiner*—Karen Cochrane Carlson
(74) *Attorney, Agent, or Firm*—Sughrue Mion, PLLC

(57) ABSTRACT

An object of the present invention is to provide a novel means for stably and surely inducing cell apoptosis using the c-myc gene as a target. The present invention relates to an apoptosis-inducing agent containing a protein that interacts with an FBP protein or a polynucleotide encoding the protein as an active ingredient and a method for inducing apoptosis, which comprises a step of causing the apoptosis-inducing agent to come into contact with cells.

2 Claims, 12 Drawing Sheets

(9 of 12 Drawing Sheet(s) Filed in Color)

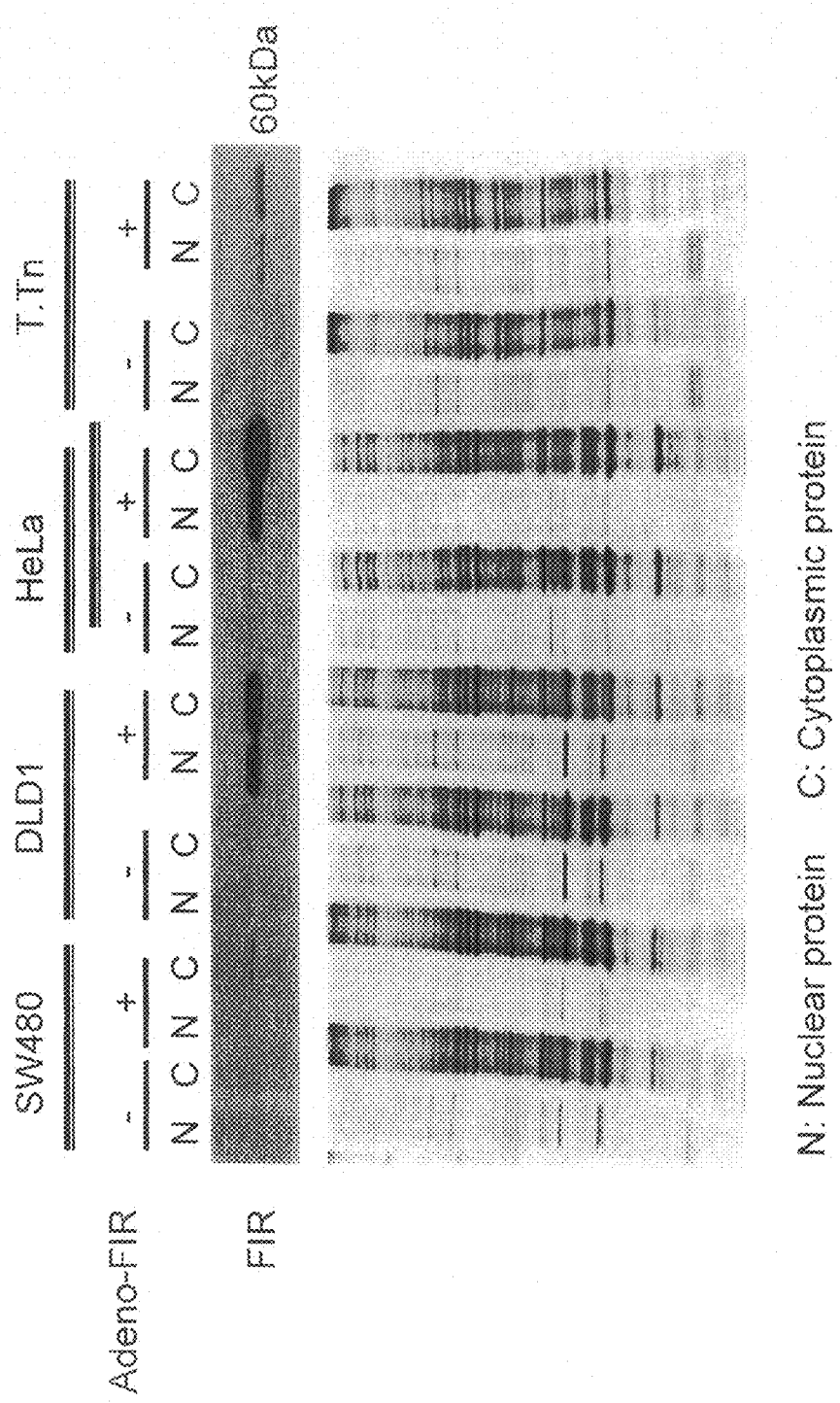

SEQUENCE LISTING

```
<160> NUMBER OF SEQ ID NOS: 14

<210> SEQ ID NO 1
<211> LENGTH: 1853
<212> TYPE: DNA
<213> ORGANISM: Homo sapiens
<220> FEATURE:
<221> NAME/KEY: CDS
<222> LOCATION: (65)..(1693)
<300> PUBLICATION INFORMATION:
<301> AUTHORS: Liu, J. et al.
<302> TITLE: Defective interplay of activators with TFIH in xerderma
      pigmentosum
<303> JOURNAL: Cell
<304> VOLUME: 104
<305> ISSUE: 3
<306> PAGES: 353-353
<307> DATE: 2001
<308> DATABASE ACCESSION NUMBER: GenBank/NM_14281
<309> DATABASE ENTRY DATE: 2001-12-26
<313> RELEVANT RESIDUES: 1 TO 1853

<400> SEQUENCE: 1
atcgcgcgag acagcggaag gagcaagagt gggaggcgcg cgcggaggcc gcgacggacg      60 caag atg gcg acg gcg acc ata gct ctc cag gtc aat ggc cag caa gga     109
     Met Ala Thr Ala Thr Ile Ala Leu Gln Val Asn Gly Gln Gln Gly
     1               5                  10                  15 ggg ggg tcc gag ccg gcg gcg gcg gcg gca gtg gtg gca gcg gga gac     157
Gly Gly Ser Glu Pro Ala Ala Ala Ala Val Val Ala Ala Gly Asp
                20                  25                  30 aaa tgg aaa cct cca cag ggc aca gac tcc atc aag atg gag aac ggg     205
Lys Trp Lys Pro Pro Gln Gly Thr Asp Ser Ile Lys Met Glu Asn Gly
             35                  40                  45 cag agc aca gcc gcc aag ctg ggg ctg cct ccc ctg acg ccc gag cag     253
Gln Ser Thr Ala Ala Lys Leu Gly Leu Pro Pro Leu Thr Pro Glu Gln
         50                  55                  60 cag gag gcc ctt cag aag gcc aag aag tac gcc atg gag cag agc atc     301
Gln Glu Ala Leu Gln Lys Ala Lys Lys Tyr Ala Met Glu Gln Ser Ile
     65                  70                  75
```

-continued

| | | |
|---|---|---|
| aag agt gtg ctg gtg aag cag acc atc gcg cac cag cag cag cag ctc<br>Lys Ser Val Leu Val Lys Gln Thr Ile Ala His Gln Gln Gln Gln Leu<br>80                 85                90                 95 | 349 |
| acc aac ctg cag atg gcg gct cag cgg cag cgg gcg ctg gcc atc atg<br>Thr Asn Leu Gln Met Ala Ala Gln Arg Gln Arg Ala Leu Ala Ile Met<br>                     100                  105                  110 | 397 |
| tgc cgc gtc tac gtg ggc tct atc tac tat gag ctg ggg gag gac acc<br>Cys Arg Val Tyr Val Gly Ser Ile Tyr Tyr Glu Leu Gly Glu Asp Thr<br>              115                  120                125 | 445 |
| atc cgc cag gcc ttt gcc ccc ttt ggc ccc atc aag agc atc gac atg<br>Ile Arg Gln Ala Phe Ala Pro Phe Gly Pro Ile Lys Ser Ile Asp Met<br>          130                135                 140 | 493 |
| tcc tgg gac tcc gtc acc atg aag cac aag ggc ttt gcc ttc gtg gag<br>Ser Trp Asp Ser Val Thr Met Lys His Lys Gly Phe Ala Phe Val Glu<br>145                 150                  155 | 541 |
| tat gag gtc ccc gaa gct gca cag ctg gcc ttg gag cag atg aac tcg<br>Tyr Glu Val Pro Glu Ala Ala Gln Leu Ala Leu Glu Gln Met Asn Ser<br>160                 165                170              175 | 589 |
| gtg atg ctg ggg ggc agg aac atc aag gtg ggc aga ccc agc aac ata<br>Val Met Leu Gly Gly Arg Asn Ile Lys Val Gly Arg Pro Ser Asn Ile<br>                    180                  185                190 | 637 |
| ggg cag gcc cag ccc atc ata gac cag ttg gct gag gag gca cgg gcc<br>Gly Gln Ala Gln Pro Ile Ile Asp Gln Leu Ala Glu Glu Ala Arg Ala<br>                195                  200                205 | 685 |
| ttc aac cgc atc tac gtg gcc tct gtg cac cag gac ctc tca gac gat<br>Phe Asn Arg Ile Tyr Val Ala Ser Val His Gln Asp Leu Ser Asp Asp<br>          210                215                 220 | 733 |
| gac atc aag agc gtg ttt gag gcc ttt ggc aag atc aag tcc tgc aca<br>Asp Ile Lys Ser Val Phe Glu Ala Phe Gly Lys Ile Lys Ser Cys Thr<br>225                 230                  235 | 781 |
| ctg gcc cgg gac ccc aca act ggc aag cac aag ggc tac ggc ttc att<br>Leu Ala Arg Asp Pro Thr Thr Gly Lys His Lys Gly Tyr Gly Phe Ile<br>240                 245                250              255 | 829 |
| gag tac gag aag gcc cag tcg tcc caa gat gct gtg tct tcc atg aac<br>Glu Tyr Glu Lys Ala Gln Ser Ser Gln Asp Ala Val Ser Ser Met Asn<br>                    260                  265                270 | 877 |
| ctc ttt gac ctg ggt ggc cag tac ttg cgg gtg ggc aag gct gtc aca<br>Leu Phe Asp Leu Gly Gly Gln Tyr Leu Arg Val Gly Lys Ala Val Thr<br>               275                  280                285 | 925 |
| ccg ccc atg ccc cta ctc aca cca gcc acg cct gga ggc ctc cca cct<br>Pro Pro Met Pro Leu Leu Thr Pro Ala Thr Pro Gly Gly Leu Pro Pro<br>          290                295                 300 | 973 |
| gcc gct gct gtg gca gct gct gca gcc act gcc aag atc aca gct cag<br>Ala Ala Ala Val Ala Ala Ala Ala Thr Ala Lys Ile Thr Ala Gln<br>305                 310                  315 | 1021 |
| gaa gca gtg gcc gga gca gcg gtg ctg ggt acc ctg ggc aca cct gga<br>Glu Ala Val Ala Gly Ala Ala Val Leu Gly Thr Leu Gly Thr Pro Gly<br>320                 325                330              335 | 1069 |
| ctg gtg tcc cca gca ctg acc ctg gcc cag ccc ctg ggc act ttg ccc<br>Leu Val Ser Pro Ala Leu Thr Leu Ala Gln Pro Leu Gly Thr Leu Pro<br>               340                  345                350 | 1117 |
| cag gct gtc atg gct gcc cag gca cct gga gtc atc aca ggt gtg acc<br>Gln Ala Val Met Ala Ala Gln Ala Pro Gly Val Ile Thr Gly Val Thr<br>              355                  360                365 | 1165 |
| cca gcc cgt cct cct atc ccg gtc acc atc ccc tcg gtg gga gtg gtg<br>Pro Ala Arg Pro Pro Ile Pro Val Thr Ile Pro Ser Val Gly Val Val<br>          370                375                 380 | 1213 |
| aac ccc atc ctg gcc agc cct cca acg ctg ggt ctc ctg gag ccc aag<br>Asn Pro Ile Leu Ala Ser Pro Pro Thr Leu Gly Leu Leu Glu Pro Lys<br>385                 390                  395 | 1261 |

-continued

```
aag gag aag gaa gaa gag gag ctg ttt ccc gag tca gag cgg cca gag    1309
Lys Glu Lys Glu Glu Glu Glu Leu Phe Pro Glu Ser Glu Arg Pro Glu
400                 405                 410                 415 atg ctg agc gag cag gag cac atg agc atc tcg ggc agt agc gcc cga    1357
Met Leu Ser Glu Gln Glu His Met Ser Ile Ser Gly Ser Ser Ala Arg
            420                 425                 430 cac atg gtg atg cag aag ctg ctc cgc aag cag gag tct aca gtg atg    1405
His Met Val Met Gln Lys Leu Leu Arg Lys Gln Glu Ser Thr Val Met
        435                 440                 445 gtt ctg cgc aac atg gtg gac ccc aag gac atc gat gat gac ctg gaa    1453
Val Leu Arg Asn Met Val Asp Pro Lys Asp Ile Asp Asp Asp Leu Glu
    450                 455                 460 ggg gag gtg aca gag gag tgt ggc aag ttc ggg gcc gtg aac cgc gtc    1501
Gly Glu Val Thr Glu Glu Cys Gly Lys Phe Gly Ala Val Asn Arg Val
465                 470                 475 atc atc tac caa gag aaa caa ggc gag gag gag gat gca gaa atc att    1549
Ile Ile Tyr Gln Glu Lys Gln Gly Glu Glu Glu Asp Ala Glu Ile Ile
480                 485                 490                 495 gtc aag atc ttt gtg gag ttt tcc ata gcc tct gag act cat aag gcc    1597
Val Lys Ile Phe Val Glu Phe Ser Ile Ala Ser Glu Thr His Lys Ala
            500                 505                 510 atc cag gcc ctc aat ggc cgc tgg ttt gct ggc cgc aag gtg gtg gct    1645
Ile Gln Ala Leu Asn Gly Arg Trp Phe Ala Gly Arg Lys Val Val Ala
        515                 520                 525 gaa gtg tac gac cag gag cgt ttt gat aac agt gac ctc tct gcg tga    1693
Glu Val Tyr Asp Gln Glu Arg Phe Asp Asn Ser Asp Leu Ser Ala
    530                 535                 540 cagtggtccc tctccccgga cttgcacttg ttccttgttt cctctgggtt ttatagtgat    1753
acagtggtgt ccccgggcc aggcgcgctc tgcccagccc agcctacagt gcggataaag    1813
gtgcggatgc tgctggccct gaaaaaaaaa aaaaaaaaa                          1853

<210> SEQ ID NO 2
<211> LENGTH: 542
<212> TYPE: PRT
<213> ORGANISM: Homo sapiens

<400> SEQUENCE: 2

Met Ala Thr Ala Thr Ile Ala Leu Gln Val Asn Gly Gln Gln Gly Gly
1               5                   10                  15

Gly Ser Glu Pro Ala Ala Ala Ala Val Ala Ala Gly Asp Lys
            20                  25                  30

Trp Lys Pro Pro Gln Gly Thr Asp Ser Ile Lys Met Glu Asn Gly Gln
        35                  40                  45

Ser Thr Ala Ala Lys Leu Gly Leu Pro Pro Leu Thr Pro Glu Gln Gln
    50                  55                  60

Glu Ala Leu Gln Lys Ala Lys Lys Tyr Ala Met Glu Gln Ser Ile Lys
65                  70                  75                  80

Ser Val Leu Val Lys Gln Thr Ile Ala His Gln Gln Gln Gln Leu Thr
                85                  90                  95

Asn Leu Gln Met Ala Ala Gln Arg Gln Arg Ala Leu Ala Ile Met Cys
            100                 105                 110

Arg Val Tyr Val Gly Ser Ile Tyr Tyr Glu Leu Gly Glu Asp Thr Ile
        115                 120                 125

Arg Gln Ala Phe Ala Pro Phe Gly Pro Ile Lys Ser Ile Asp Met Ser
    130                 135                 140

Trp Asp Ser Val Thr Met Lys His Lys Gly Phe Ala Phe Val Glu Tyr
145                 150                 155                 160
```

```
Glu Val Pro Glu Ala Ala Gln Leu Ala Leu Glu Gln Met Asn Ser Val
                165                 170                 175

Met Leu Gly Gly Arg Asn Ile Lys Val Gly Arg Pro Ser Asn Ile Gly
            180                 185                 190

Gln Ala Gln Pro Ile Ile Asp Gln Leu Ala Glu Ala Arg Ala Phe
        195                 200                 205

Asn Arg Ile Tyr Val Ala Ser Val His Gln Asp Leu Ser Asp Asp
    210                 215                 220

Ile Lys Ser Val Phe Glu Ala Phe Gly Lys Ile Lys Ser Cys Thr Leu
225                 230                 235                 240

Ala Arg Asp Pro Thr Thr Gly Lys His Lys Gly Tyr Gly Phe Ile Glu
                245                 250                 255

Tyr Glu Lys Ala Gln Ser Ser Gln Asp Ala Val Ser Ser Met Asn Leu
                260                 265                 270

Phe Asp Leu Gly Gly Gln Tyr Leu Arg Val Gly Lys Ala Val Thr Pro
            275                 280                 285

Pro Met Pro Leu Leu Thr Pro Ala Thr Pro Gly Gly Leu Pro Pro Ala
    290                 295                 300

Ala Ala Val Ala Ala Ala Ala Thr Ala Lys Ile Thr Ala Gln Glu
305                 310                 315                 320

Ala Val Ala Gly Ala Ala Val Leu Gly Thr Leu Gly Thr Pro Gly Leu
                325                 330                 335

Val Ser Pro Ala Leu Thr Leu Ala Gln Pro Leu Gly Thr Leu Pro Gln
            340                 345                 350

Ala Val Met Ala Ala Gln Ala Pro Gly Val Ile Thr Gly Val Thr Pro
        355                 360                 365

Ala Arg Pro Pro Ile Pro Val Thr Ile Pro Ser Val Gly Val Val Asn
    370                 375                 380

Pro Ile Leu Ala Ser Pro Pro Thr Leu Gly Leu Leu Glu Pro Lys Lys
385                 390                 395                 400

Glu Lys Glu Glu Glu Glu Leu Phe Pro Glu Ser Glu Arg Pro Glu Met
                405                 410                 415

Leu Ser Glu Gln Glu His Met Ser Ile Ser Gly Ser Ser Ala Arg His
            420                 425                 430

Met Val Met Gln Lys Leu Leu Arg Lys Gln Glu Ser Thr Val Met Val
        435                 440                 445

Leu Arg Asn Met Val Asp Pro Lys Asp Ile Asp Asp Leu Glu Gly
    450                 455                 460

Glu Val Thr Glu Glu Cys Gly Lys Phe Gly Ala Val Asn Arg Val Ile
465                 470                 475                 480

Ile Tyr Gln Glu Lys Gln Gly Glu Glu Asp Ala Glu Ile Ile Val
                485                 490                 495

Lys Ile Phe Val Glu Phe Ser Ile Ala Ser Glu Thr His Lys Ala Ile
            500                 505                 510

Gln Ala Leu Asn Gly Arg Trp Phe Ala Gly Arg Lys Val Val Ala Glu
        515                 520                 525

Val Tyr Asp Gln Glu Arg Phe Asp Asn Ser Asp Leu Ser Ala
    530                 535                 540

<210> SEQ ID NO 3
<211> LENGTH: 18
<212> TYPE: DNA
<213> ORGANISM: Artificial Sequence
```

```
<220> FEATURE:
<223> OTHER INFORMATION: Description of Artificial Sequence: synthetic
      DNA

<400> SEQUENCE: 3
ggccccatca agagcatg                                                    18

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 4
ggggctgggc cagggtcag                                                   19

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 5
gcacctggag tcatcaca                                                    18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 6
cgcagaacca tcactgtag                                                   19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 7
ggagtctaca gtgatggttc                                                  20

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 8
tcctggtcgt acacttca                                                    18

<210> SEQ ID NO 9
<211> LENGTH: 18
<212> TYPE: DNA
<213> ORGANISM: Artificial Sequence
```

```
<220> FEATURE:
<223> OTHER INFORMATION: Description of Artificial Sequence: synthetic
      DNA

<400> SEQUENCE: 9
gcctcagagt gcatcgac                                                 18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 10
tccacagaaa caacatcg                                                 18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 11
tggagaaaat ctggcaccac                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 12
aatggtgatg acctggccgt                                               20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 13
agacagcgga aggagcaaga gtgg                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 14
ctgtgcagct tcggggacct cata                                          24
```

APOPTOSIS-INDUCING AGENT AND METHOD FOR INDUCING APOPTOSIS

CROSS-REFERENCE TO RELATED APPLICATIONS

This application is a divisional of U.S. application Ser. No. 10/554,026 (Confirmation No. 1874) filed Oct. 21, 2005, now abandoned, which is a National Stage Application of PCT//JP04/04516, filed Mar. 30, 2004, which claims the benefit of Japanese Patent Application No. 2003-116299 filed Apr. 21, 2003, the disclosure of each is incorporated by reference in its entirety.

TECHNICAL FIELD

The present invention relates to an apoptosis-inducing agent and a method for inducing apoptosis. More specifically, the present invention relates to a drug for inducing apoptosis in cells (e.g., cancer cells), the existence of which is harmful to their host animals, a method for inducing apoptosis using the drug, and a method for treating cancer using the drug.

BACKGROUND ART

Apoptosis is cell death resulting from cells' own active induction under physiological conditions. Apoptosis is clearly distinguished from cell death (necrosis) resulting from environmental deterioration. Apoptosis is morphologically characterized by chromosome aggregation in cell nuclei, fragmentation of cell nuclei, disappearance of microvillus on the cell surface layers, aggregation of cytoplasm, and the like. When cells initiate apoptosis, they become atrophied. Intracellular contents are immediately incorporated by macrophages and surrounding cells without being released outside the cells. Thus, inflammation is not induced and the surrounding cells are not affected by apoptosis. Hence, many attempts have been made to treat disease by inducing apoptosis in cells (e.g., cancer cells), the existence of which is harmful to their host organisms.

As means or factors for inducing apoptosis, glucocorticoid treatment, cell damage due to cytotoxic-T cells, atrophy of hormone-dependent tissues, radiation exposure, NK cells, killer cells, tumor necrosis factors (TNF), cytokines such as lymphotoxin (LT), and the like have been reported (Wyllie, A. H., Nature 284: 555-556, 1986; Wyllie, A. H. et al., Int. Rev. Cytol. 68: 251, 1980; Duvall, E. and Wyllie, A. H., Immunology Today, 7: 115-119, 1986; Sellins, K. S. et al., J. Immunol. 139: 3199, 1987; Yamada, T. et al., Int. J. Radiat. Biol. 53: 65, 1988; Schmid, D. S. et al., Proc. Natl. Acad. Sci. USA, 83: 1881-1885, 1986; John, C. et al., J. Immunol. 129 (4): 1782-1787, 1982; Howell, D. M. et al., J. Immunol. 140: 689-692, 1988; Gillian, B. et al., Eur. J. Immunol. 17: 689-693, 1987). Furthermore, it is also known that apoptosis is also induced by some types of antibody (e.g., anti-CD3 antibody and anti-APO-I antibody) (Trauth, B. C. et al., Science 245: 301-305, 1989; Smith, C. A. et al., Nature 337: 181-184, 1989; Tadakuma, T. et al., Eur. J, Immunol. 20: 779, 1990). Moreover, it has also been reported that cycloheximide, a protein synthesis inhibitor, induces apoptosis in acute leukemia cells, that actinomycin D, an RNA synthesis inhibitor, induces apoptosis in small intestine crypt cells, and that both inhibitors induce apoptosis in HL-60 cells (Martin, S. J. et al., J. Immunol. 145: 1859-1867, 1990).

As apoptosis-related therapeutic methods, in addition to the above attempts to treat cancer using an anti-Apo-I antibody, administration of etoposide or aclarubicin against osteomyelodysplasia syndrome (MDS) due to active proliferation of blast cells has been examined (Shibuya, T., J. Clinical and Experimental Medicine 160 (5): 319-323, 1992). In addition to these attempts, inventions relating to methods for inducing apoptosis or drug compositions therefor are known (e.g., JP Patent Publication (Kokai) No. 2001-275681 A; JP Patent Publication (Kohyo) No. 2002-526109 A; JP Patent Publication (Kohyo) No. 10-508575 A; JP Patent Publication (Kokai) No. 9-328425 A; and International Patent Publication WO95/28154 Pamphlet).

In addition, c-Myc protein encoded by the c-myc gene is not only extremely important in cell life activities such as cell proliferation, cell differentiation, and the cell cycle, but is also deeply involved in cellular tumorigensis (transformation). Enhanced c-Myc protein expression is observed in many cancer tissues and in cellular tumorigensis due to the activation of the c-myc gene. c-Myc protein also relates to apoptosis. Both increases and decreases in intracellular expression level of c-Myc protein induce apoptosis (Thompson, E. B. Ann. Rev. Physiol. 60: 575-600, 1998). For example, the suppression of the c-myc gene was found to be essential for apoptosis induction in experiments using glucocorticoid in human leukemia cells (Thulasi, R. et al., J. Biol. Chem. 268: 18306-18312, 1993; Zhou, F. et al., J. Steroid Biochem. Mol. Biol. 73:195-202, 2000; Thompson, E. A. et al., Cancer Res., 51: 5544-5550, 1991; Helmberg, A. et al., EMBO J., 14: 452-60, 1995). In systems using B cells, all chemical substances that induce apoptosis are deeply associated with the suppression of c-myc gene expression (McCormack, J. E. et al., Proc. Natl. Acad. Sci. U.S.A. 81:5546-5550, 1984; Sonenshein, G. E., J. Immunol. 158: 1994-1997, 1997; Fischer, G. et al., J. Exp. Med., 179: 221-228, 1994; Wu, M. et al., Mol. Cell. Biol. 16: 5015-5025, 1996). Furthermore, apoptosis is induced by introduction of an antisense oligonucleotide of c-myc into several types of cell (Thompson, E. B., Ann. Rev. Physiol. 60: 575-600, 1998). In addition, apoptosis is induced by depletion of IL-3 in IL-3-dependent myeloma cells and simultaneous forced expression of the c-myc gene (Askew, D. S. et al., Oncogene 6: 1915-1922, 1991). Moreover, apoptosis is induced by forced expression of the c-myc gene in Rat1 fibroblasts in serum-free media (Evan, G. I. et al., Cell 69: 119-128, 1992).

Such c-Myc protein is produced by transcription of the c-myc gene. The c-myc gene is tightly controlled by many transcription factors, but how transcription is controlled is mostly unknown. For example, an abnormal APC (adenomatous polyposis coli) gene is observed in 70% to 80% of colorectal cancer cases. It is said that such abnormality is developed at the most initial stage of oncogenesis. APC protein binds to β-catenin that is stabilized by the Wnt/Wingless signal transduction pathway, thereby suppressing the functions thereof. β-catenin binds to the Tcf/Lef transcription factor, thereby activating c-myc gene transcription. Hence, it is considered that when abnormalities take place in an APC gene, it becomes impossible to suppress β-catenin activities and the c-myc gene is sustainably activated, thereby inducing cell proliferation.

c-Myc protein expression is under influence of many transcription factors, in addition to the Wnt/Wingless signal transduction pathway. For example, it is known that differentiation of HL60 (human promyeloid leukemia cell) is induced by various chemical substances including DMSO (Dimethyl sulfoxide; Me2SO), retinoic acid, phorbol esters, vitamin D derivatives, and the like. At the time of differentiation, it is known that intracellular c-Myc protein expression is attenuated. These facts suggest that various differentiation-inducing substances activate various transcription factors so as to affect the c-myc gene and that such activations are finally integrated into a single pathway so as to suppress c-myc gene transcription.

Based on such understandings, analysis has been carried out regarding which site located upstream of the c-myc gene affects the transcription. As a result, it has been shown that a site of a hundred and several tens of nucleotides, which is located as far as 1.5 kb upstream of the transcription initiation site of the c-myc gene, is extremely important in c-myc gene transcription. The site has been named FUSE (Far Upstream Element) (Avigan, M. et al., J. Biol. Chem., 265: 18538-18545, 1990). Next, protein that binds to FUSE has been analyzed by oligonucleotide affinity chromatography. Thus, FBP (FUSE-binding protein) having a molecular weight of 70 kDa has been identified. Furthermore, the FBP protein has its own strong transcriptional activity. It is shown that the FBP protein may control the c-myc gene (Bazar, L. et al., J. Biol. Chem., 270: 8241-8248, 1995; Duncan, R. et al., Genes Dev., 8:465-480, 1994; Michelotti, G. A. et al., Mol. Cell. Biol. 16:2656-2669, 1996). Moreover, FIR (FBP Interacting Repressor) has been identified as protein that binds to (interacts with) the FBP protein (Liu, J. et al., Mol. Cell, 5: 331-341, 2000). Such FIR has been shown to suppress c-myc gene transcription by suppressing the functions of a basic transcription factor TFIIH (Liu, J. et al., Cell, 104: 353-363, 2001). However, FIR has never been known to induce apoptosis.

As described above, c-Myc protein is deeply involved in carcinogenesis and apoptosis of the cell. It is expected that it may be possible to destroy cancer cells by controlling the expression of c-Myc protein. However, as described above, c-Myc protein causes apoptosis in cases of both expression level increases and decreases. Thus, it is not easy to induce apoptosis by controlling the expression of c-Myc protein. Furthermore, a method using glucocorticoid or an antisense strand of the c-myc gene as a means for inducing apoptosis by suppressing c-Myc protein expression has been proposed (Thompson, E. B., Ann. Rev. Physiol. 60: 575-600, 1998; Thulasi, R., et al., J. Biol. Chem. 268: 18306-18312, 1993; Zhou, F. et al., J. Steroid Biochem. Mol. Biol. 73:195-202, 2000; Thompson, E. A. et al., Cancer Res., 51: 5544-5550, 1991; Helmberg, A. et al., EMBO J., 14: 452-60, 1995). However, such method is not preferable for clinical use in terms of side effects and stable effects.

Therefore, an object of the present invention is to provide a novel means for stably and surely inducing cell apoptosis using the c-myc gene as a target.

Another object of the present invention is to provide a method for inducing apoptosis in cells within animal individuals, and particularly cells, the existence of which is harmful to their host animals, using the above means for inducing apoptosis.

SUMMARY OF THE INVENTION

As a result of intensive studies to achieve the above objects, we have discovered that an FIR (FBP Interacting Repressor) protein that interacts with a FUSE-binding protein (hereinafter, referred to as "FBP protein") binding to single-strand DNA called FUSE (Far Upstream Element), located upstream of the c-myc gene promoter, suppresses the expression of c-Myc protein and can induce apoptosis. Thus, we have completed the present invention.

The present invention encompasses the following inventions.

(1) An apoptosis-inducing agent, which contains a protein that interacts with an FBP protein as an active ingredient.

(2) The apoptosis-inducing agent according to (1), wherein the protein interacting with the FBP protein is:

a protein consisting of the amino acid sequence represented by SEQ ID NO: 2 in the sequence listing;

a protein consisting of an amino acid sequence derived from the amino acid sequence represented by SEQ ID NO: 2 in the sequence listing by deletion, substitution, or addition of one or several amino acids and having apoptosis-inducing activity; or a partial peptide thereof.

(3) An apoptosis-inducing agent, which contains a polynucleotide encoding a protein that interacts with an FBP protein as an active ingredient.

(4) The apoptosis-inducing agent according to (3), wherein the polynucleotide encoding the protein that interacts with the FBP protein is: a polynucleotide consisting of the nucleotide sequence represented by SEQ ID NO: 1 in the sequence listing;

a polynucleotide hybridizing under stringent conditions to a polynucleotide consisting of a nucleotide sequence complementary to the polynucleotide consisting of the nucleotide sequence represented by SEQ ID NO: 1 in the sequence listing and encoding a protein having apoptosis-inducing activity; or a partial fragment thereof.

(5) The apoptosis-inducing agent according to any one of (1) to (4), which has a form that allows it to be introduced into a cell.

(6) The apoptosis-inducing agent according to (5), wherein the form that allows introduction into a cell is a vector.

(7) The apoptosis-inducing agent according to any one of (1) to (6), which is used for treating cancer.

(8) A method for inducing apoptosis, which is a method for inducing apoptosis in a cell that proliferates due to the expression of a c-myc gene and which comprises a step of causing the apoptosis-inducing agent according to any one of (1) to (7) to come into contact with the cell.

(9) The method according to (8), wherein the cell is a cancer cell.

(10) The method according to (8) or (9), wherein the cell is a cell within a mammalian body.

(11) The method according to (10), wherein the mammal is a human.

(12) A method for treating cancer, wherein an effective dose of: a protein consisting of the amino acid sequence represented by SEQ ID NO: 2 in the sequence listing; a protein consisting of an amino acid sequence derived from the amino acid sequence represented by SEQ ID NO: 2 in the sequence listing by deletion, substitution, or addition of 1 or several amino acids and having apoptosis-inducing activity; or a partial peptide thereof is administered to a mammal.

(13) A method for treating cancer, wherein an effective dose of: a polynucleotide consisting of the nucleotide sequence represented by SEQ ID NO: 1 in the sequence listing; a polynucleotide hybridizing under stringent conditions to a polynucleotide consisting of a nucleotide sequence complementary to the polynucleotide consisting of the nucleotide sequence represented by SEQ ID NO: 1 in the sequence listing and encoding a protein having apoptosis-inducing activity; or a fragment thereof is administered to a mammal.

(14) The method according to (12) or (13), wherein the mammal is a human.

Furthermore, in the present invention, "protein that interacts with FBP protein" means a protein that binds to the FBP protein and acts to suppress the functions of the FBP protein (specifically, the transcriptional activity of c-myc gene).

Furthermore, "form (of a polynucleotide) that allows introduction into a cell" means a form that enables expression of a protein or a peptide encoded by a polynucleotide that has been introduced into a cell.

Furthermore, "protein" and "peptide" mean molecules that are composed of a plural number of amino acid residues binding to each other through amide linkage (peptide linkage). "Polynucleotide" means a molecule comprising 100 or more phosphate esters of nucleosides (ATP, GTP, CTP, and UTP; or dATP, dGTP, dCTP, and dTTP), wherein purine or pyrimidine binds to sugar through β-N-glycosidic linkage. "Oligonucleotide" means a molecule wherein 2 to 99 such phosphate esters are linked.

Other terms and concepts in the present invention are defined in detail in the explanations of the embodiments and the examples of the invention. Moreover, various techniques employed to implement the present invention can be easily and surely implemented by persons skilled in the art based on known literature and the like except for particular techniques, the sources of which are clearly shown. For example, the preparation of drugs that can be used for treatment methods and the like of the present invention is described in Remington's Pharmaceutical Sciences, 18th Edition, ed. A. Gennaro, Mack Publishing Co., Easton, Pa., 1990. Genetic engineering techniques and molecular biological techniques are described in, for example, Sambrook and Maniatis, Molecular Cloning-A Laboratory Manual, Cold Spring Harbor Laboratory Press, New York, 1989; and Ausubel, F. M. et al., Current Protocols in Molecular Biology, John Wiley & Sons, New York, N.Y., 1995.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 12 shows FIR protein expression within nuclei and the same in cytoplasm in colorectal cancer (SW480 and DLD1) cell lines, a cervical cancer (HeLa) cell line, and an esophageal cancer (T.Tn) cell line after infection with an FIR adenovirus vector, as analyzed by immunoblotting.

Figure 1:
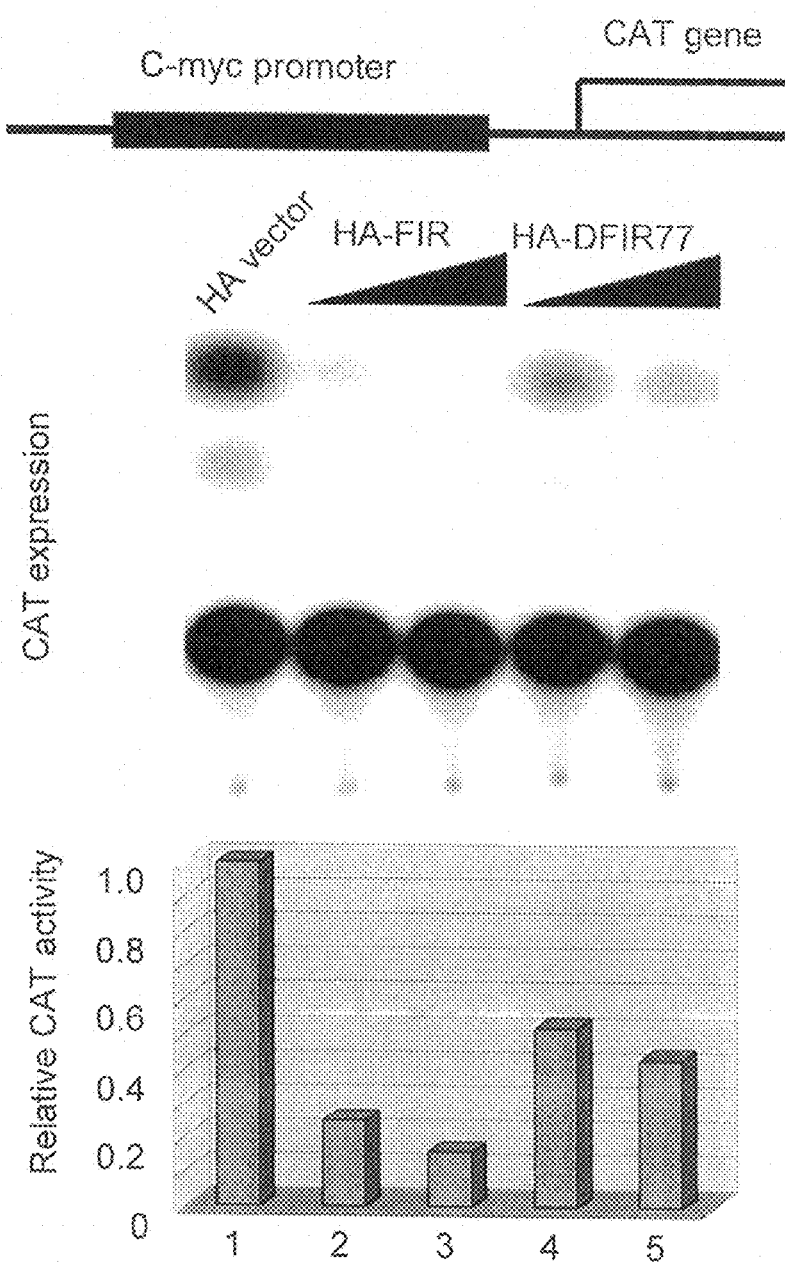
FIG. 1 shows the result of CAT assay by which examination concerning whether or not an FIR protein has ability to suppress c-myc transcription was carried out.

The present invention is explained in detail as follows. This application claims priority of Japanese patent application No. 2003-116299 filed on Apr. 21, 2003, and encompasses the content described in the specification and/or drawings of this patent application.

1. Apoptosis-Inducing Agent

The apoptosis-inducing agent of the present invention contains as an active ingredient a protein that interacts with an FBP protein or a polynucleotide encoding a protein that interacts with the FBP protein, wherein such protein or polynucleotide is in a form that can be introduced into a cell.

Examples of the above protein that interacts with an FBP protein, preferably a human FBP protein include a human FIR protein (Liu, J. et al., Mol. Cell, 5: 331-341, 2000; Liu, J. et al., Cell, 104: 353-363, 2001; and GenBank/NM_14281), human SIAHBP1 (siah binding protein 1: GenBank/BC008875), a transcription variant 1 of human SIAHBP1 (GenBank/NM_078480), and a transcription variant 2 of human SIAHBP1 (GenBank/NM_014281). Among these proteins, a human FIR protein having the amino acid sequence represented by SEQ ID NO: 2 is particularly preferable.

Examples of such human FIR protein that is used in the present invention also include a protein consisting of an amino acid sequence derived from the amino acid sequence represented by SEQ ID NO: 2 by deletion, substitution, or addition of 1 or several amino acids and having apoptosis-inducing activity.

Here, the number of amino acids that may be deleted, substituted, or added is preferably 1 to several amino acids. For example, 1 to 10 amino acids and preferably 1 to 5 amino acids may be deleted from the amino acid sequence represented by SEQ ID NO: 2, 1 to 10 amino acids and preferably 1 to 5 amino acids may be added to the amino acid sequence represented by SEQ ID NO: 2, or 1 to 10 amino acids and preferably 1 to 5 amino acids may be substituted with other amino acids in the amino acid sequence represented by SEQ ID NO: 2.

Deletion, addition, and substitution of amino acids can be carried out by alteration of genes encoding the above proteins by techniques known in the relevant technical field. Mutations can be introduced into genes by known techniques such as the Kunkel method, or the Gapped duplex method, or a method according thereto. For example, mutations are introduced using a kit for introducing mutations that uses the site-directed mutagenesis method (e.g., Mutant-K (produced by TAKARA BIO INC.) or Mutant-G (produced by TAKARA BIO INC.)) or using an LA PCR in vitro Mutagenesis series kit (TAKARA BIO INC.).

Here, "apoptosis-inducing activity" means activity to cause cells to shrink and to cause nuclei to become fragmented. This activity can be confirmed by, for example, introducing a gene into HeLa cells or the like, causing overexpression of the gene, observing morphological changes of the cells, and performing FACS analysis.

Furthermore, "having apoptosis-inducing activity" means possession of activity that is substantially equivalent to that retained by a protein having the amino acid sequence represented by SEQ ID NO: 2.

A peptide (also referred to as partial peptide) containing a partial amino acid sequence in the above protein is also encompassed in the scope of the present invention. The number of amino acids composing such partial peptide is at least 10 or more, preferably 30 or more, and more preferably 80 or more.

The above protein or partial peptide thereof can be provided, if necessary, in the form of a salt and preferably in the form of a physiologically acceptable acid addition salt. Examples of such salt include a salt of inorganic acid (e.g., hydrochloric acid, phosphoric acid, hydrobromic acid, or sulfuric acid) and a salt of organic acid (e.g., acetic acid, formic acid, propionic acid, fumaric acid, maleic acid, succinic acid, tartaric acid, citric acid, malic acid, oxalic acid, benzoic acid, methanesulfonic acid, or benzenesulfonic acid).

The above protein can be obtained by, for example, a method that involves chemically synthesizing such protein based on a known amino acid sequence (e.g., in the case of FIR protein, the amino acid sequence of SEQ ID NO: 2), in vitro transcription from expression vectors, and a method that involves isolating and purifying such protein as an expression product of cells transformed with expression vectors. For example, when a protein is expressed by in vitro translation, such protein can be produced in vitro by adding an expression vector having an RNA polymerase promoter to an in vitro translation system such as a rabbit reticulocyte lysate or a wheat germ extract containing RNA polymerase corresponding to the promoter. Examples of an RNA polymerase promoter include T7, T3, and SP6. Examples of vectors containing these RNA polymerase promoters include pKA1, pCDM8, pT3/T7 18, pT7/3 19, and pBluescript II. Furthermore, when a, protein is expressed in microorganisms such as Escherichia coli, an expression vector is prepared by recombining an expression vector (having a replication origin derived from microorganisms, a promoter, a ribosome-binding site, a DNA cloning site, a terminator, and the like) with a DNA fragment encoding the protein. Through transformation of host cells with the expression vector, transformant cells expressing the protein can be obtained. Through culture of such transformants, the target protein can be produced in large quantities from the culture products. Examples of an expression vector for Escherichia coli include a pUC system, pBluescript II, a pET expression system, and a pGEX expression system. Moreover, when a protein is expressed in eukaryotic cells, a DNA fragment encoding such protein is inserted into an expression vector for eukaryotic cells having a promoter, splicing region, poly (A) addition site, and the like, thereby preparing a recombinant vector. Through introduction of such vector into eukaryotic cells, transformed eukaryotic cells expressing the target protein can be obtained. Examples of such expression vector include pKA1, pCDM8, pSVK3, pMSG, pSVL, pBK-CMV, pBK-RSV, EBV vector, pRS, and pYES2. As eukaryotic cells, for example, mammalian cultured cells such as human embryonic kidney cells HEK293, monkey kidney cells COS7, and Chinese hamster ovary cells CHO, or primary cultured cells isolated from human organs, can be used. Budding yeasts, fission yeasts, silkworm cells, Xenopus egg cells, and the like can also be used. To introduce an expression vector into cells, known methods such as an electroporation method, a calcium phosphate method, a liposome method, and a DEAE dextran method can be employed. Protein expressed in transformed cells can be isolated and purified by a combination of known separation procedures. Examples of such procedures include treatment using a denaturing agent such as urea or surfactant, ultrasonication, enzymatic digestion, salting-out, a solvent precipitation method, dialysis, centrifugation, ultrafiltration, gel filtration, SDS-PAGE, isoelectric focusing, ion exchange chromatography, hydrophobic chromatography, affinity chromatography, and reverse phase chromatography.

Furthermore, partial peptides can be produced by a known peptide synthesis method or cleavage of the above protein with appropriate peptidase (e.g., trypsin, chymotrypsin, or arginylendopeptidase). As such peptide synthesis method, for example, either a solid-phase synthesis method or a liquid-phase synthesis method may be employed.

Furthermore, as a polynucleotide that is used in the apoptosis-inducing agent of the present invention, a polynucleotide having the nucleotide sequence represented by SEQ ID NO: 1 and encoding the human FIR protein is preferable.

Examples of such polynucleotide encoding the human FIR protein that is used in the present invention include a polynucleotide hybridizing under stringent conditions to a polynucleotide consisting of a nucleotide sequence complementary to the polynucleotide consisting of the nucleotide sequence represented by SEQ ID NO: 1 and encoding a protein having apoptosis-inducing activity.

Here, stringent conditions mean conditions wherein so-called a specific hybrid is formed, but a non-specific hybrid is not formed. Under an example of such conditions, a nucleic acid with high homology, that is, the complementary strand of DNA consisting of a nucleotide sequence having 70% or more, preferably 80% or more, more preferably 90% or more, and most preferably 95% or more homology with the nucleotide sequence represented by SEQ ID NO: 1, hybridizes, but the complementary strand of a nucleic acid with homology lower than such levels does not hybridize. More specifically, such conditions comprise a sodium concentration ranging from 150 mM to 900 mM and preferably 600 mM to 900 mM and a temperature ranging from 60° C. to 68° C. and preferably of 65° C.

Genomic DNA encoding each of the above proteins, mRNA that is the transcription product of such genomic DNA, cDNA synthesized using such mRNA as a template, and the like can be used. cDNA is particularly preferable. Such cDNA can be obtained according to a known method using the above known sequences. For example, a cDNA library is synthesized using a known method (Mol. Cell. Biol. 2, 161-170, 1982; J. Gene 25, 263-269, 1983; and Gene, 150, 243-250, 1994). A target cDNA can then be isolated using a probe DNA prepared based on a known nucleotide sequence as described above (e.g., SEQ ID NO: 1 encoding the FIR protein). The thus obtained cDNA can be amplified by a generally performed gene amplification method such as a PCR (Polymerase Chain Reaction) method, a NASBN (Nucleic acid sequence based amplification) method, a TMA (Transcription-mediated amplification) method, or an SDA (Strand Displacement Amplification) method. Moreover, each cDNA can be obtained in a necessary amount by an RT-PCR method using a primer set prepared based on known sequences and mRNA isolated from human cells as a template. Such primer set can be prepared using commercial software for primer design, such as Oligo™ [produced by National Bioscience Inc. (U.S.A.)] and GENETYX [produced by Software Development Co., Ltd. (Japan)].

Examples of means to prepare the above proteins or polynucleotides in forms that can be introduced into cells are as follows.

A protein can be prepared to have a form that can be introduced into cells without changing its structure or functions by, for example, mixing protein molecules into a pharmacologically acceptable carrier solution for formulation.

Such drug can be introduced into cells, for example, into in vitro cells by a microinjection method. Alternatively, a method for introducing such drug into cells using lipids (e.g., BioPORTER (Gene Therapy Systems Inc., U.S.A.) or Chariot (Active Motif Inc., U.S.A.)) can also be employed.

As another embodiment, a protein can be prepared to have a form that can be introduced into cells by ligating a peptide that passes through a cell membrane to the N-terminal side of a protein (polypeptide) so as to prepare a fusion polypeptide. When comprising such peptide that passes through a cell membrane, the protein can passes through the cell membrane and then become incorporated into the cell. As such peptide that passes through a cell membrane, PTD (protein transduction domain) of HIV-1 TAT, PTD of *Drosophila* homeobox protein antennapedia, or the like can be used. For example, in the case of HIV-1•TAT, the amino acid sequence thereof and the nucleotide sequence of the cDNA of HIV-1•TAT are known (Science, 285: 1569-1572, 1999; GenBank Accession NO. U39362 M96155). A DNA fragment encoding a domain corresponding to the PTD (the amino acid sequence ranging from amino acid No. 47 to amino acid No. 57 of HIV•TAT) is ligated to the above cDNA so as to form a fusion DNA fragment. Through expression of the fusion DNA fragment in host cells such as *Escherichia coli*, such PTD peptide is ligated to the N-terminal side and then a fusion polypeptide can be prepared. Moreover, the PTD of antennapedia is also known (e.g., GenBank Accession No. AE001573). Thus a fusion polypeptide to which the PTD is ligated can be similarly prepared. Alternatively, a fusion polypeptide to which a peptide that passes through a cell membrane is ligated can also be prepared by a method that involves binding a polypeptide to a PTD peptide via a divalent crosslinking agent (e.g., EDC or β-alanine).

In the meantime, a polynucleotide can be prepared to have a form that can be introduced into cells by, for example, incorporating the polynucleotide into an expression vector. As such expression vector, a known expression vector for eukaryotic cells having a promoter, a splicing region, a poly (A) addition site, and the like can be used. Through insertion of a polynucleotide encoding the above polypeptide into a cloning site of the expression vector, a polypeptide expression vector can be constructed.

Such expression vector can be introduced into in vitro cells (cultured cells), by a known method such as an electroporation method, a calcium phosphate method, a liposome method, and a DEAE dextran method.

Moreover, for example, viral or non-viral vectors (means) for gene introduction can be introduced into in vivo cells (specifically, cells within animal individuals) for the purpose of promoting incorporation into cells or enhancing directivity to target cells. Drugs produced in such forms can be introduced in vivo for gene therapy (e.g., JP Patent Publication (Kokai) No. 2003-24092 A and JP Patent Publication (Kokai) No. 2003-501445 A). Examples of such viral vector include adenovirus vectors, retrovirus vectors, lentivirus vectors, AAV (adeno-associated virus) vectors, vaccinia virus vectors, human immunodeficiency virus (HIV) vectors, and herpes virus vectors. Furthermore, examples of such non-viral vector include high-molecular-weight compounds such as liposomes, artificial lipid vehicles, hollow nanoparticles, and dendrimers. In this case, commercial reagents for introduction (e.g., lipofectin, lipofectamine, or DMRIE-C (produced by Invitrogen Corporation), Metafectene or DOTAP (produced by BioTex Corporation), or a Tfx reagent (produced by Promega Corporation)) can be used.

Apoptosis is physiological cell death essential for normal cell development and/or differentiation. Apoptosis takes place in individual cells, specifically in the cell cycle of normal biological tissues. Hence, it has been revealed that an excessive decrease in apoptosis cause many functional disorders. Therefore, the apoptosis-inducing agent of the present invention can be used as an agent for treating and/or preventing disease caused by a decrease in apoptpsis. Typical examples of such disease caused by a decrease in apoptpsis include, but are not limited to, malignant tumor (e.g., gastric cancer, colorectal cancer, mammary cancer, lung cancer, esophageal cancer, prostate cancer, hepatic cancer, kidney cancer, bladder cancer, skin cancer, uterine cancer, brain tumor, osteosarcoma, or myeloma), leukemia, autoimmune disease (e.g., type I diabetes, multiple sclerosis, systemic lupus erythematodes, or chronic rheumatoid arthritis), viral infectious disease (e.g., HIV infection), and hepatitis.

The apoptosis-inducing agent of the present invention can be prepared in various forms for pharmaceutical preparations and thus can be administered orally or parenterally and systemically or locally. In the case of oral administration of such agent, the agent is formulated into tablets, capsules, granules, powders, pills, liquid preparations for internal use, suspensions, emulsions, syrups, or the like. Alternatively the agent may be formulated into a dry product that is re-dissolved when it is used. Furthermore, in the case of parenteral administration of this agent, the agent is formulated into an intravenous injection (including drip), intramuscular injection, intraperitoneal injection, subcutaneous injection, suppository, or the like. When formulated into a pharmaceutical preparation for injection, the agent is provided in a unit dose ampule or a container containing many doses of the agent.

These various pharmaceutical preparations can be produced according to conventional methods by appropriately selecting a pharmaceutically-generally-used excipient, extending agent, binder, moistening agent, disintegrating agent, lubricant, surfactant, dispersing agent, buffer agent, preservative, solubilizing agent, antiseptic agent, flavoring agent, soothing agent, stabilizer, isotonizing agent, or the like.

A dose of the apoptosis-inducing agent of the present invention differs depending on age of an administration subject, the route of administration, administration frequency, symptoms, dosage form, and the like. The therapeutically effective dose of a protein or a polypeptide ranges from approximately 0.001 to 30 mg/kg body weight, preferably approximately 0.01 to 25 mg/kg body weight, more preferably approximately 0.1 to 20 mg/kg body weight, and furthermore preferably from approximately 1 to 10 mg/kg, 2 to 9 mg/kg, 3 to 8 mg/kg, 4 to 7 mg/kg, or 5 to 6 mg/kg body weight. Such protein or polypeptide is administered once a day or several separate times per day, for a period one or more days. When such polynucleotide encoding a protein is introduced by a method such as gene therapy, a polynucleotide that can express a protein in an amount within one of the above ranges may be administered.

2. Method for Inducing Apoptosis

The method for inducing apoptosis of the present invention comprises causing the above apoptosis-inducing agent to come into contact with the cells that proliferate due to c-myc gene expression.

In addition, the c-myc gene is involved in proliferation in almost all animal cells. Thus, the method of the present invention can actually be applied to induce apoptosis in all animal cells. Particularly, the method is preferably applied to cells that have become malignant cells due to overexpression of the c-myc gene.

The method of the present invention may also be applied to in vitro cells (cultured cells) and in vivo cells (cells within animal bodies). When applied to in vitro cells, as described above, the method can be implemented by a known method for introducing a protein expression vector into cells, such as an electroporation method, a calcium phosphate method, a liposome method, or a DEAE dextran method, a method that involves microinjecting a protein's own solution into cells, a method for introducing such a solution into cells via lipids, or a method that involves causing a PTD peptide fusion protein to come into contact with cultured cells.

When applied to in vivo cells, as described above, the method can be implemented by, for example, a method for introducing a polynucleotide into in vivo cells using a method according to gene therapy, a method that involves microinjecting a protein's own solution into in vivo cells, a method for introducing such a solution into cells via lipids, or a method that involves administering a PTD peptide fusion protein solution in vivo.

Such in vivo cells may be any cells within animal individuals. Particularly, apoptosis induction for the purpose of treating cancer or the like of useful animals (e.g., domestic animals or pets) is preferable. Furthermore, apoptosis induction for the purpose of treating cancer of humans is more preferable.

3. Method for Treating Cancer

The method for treating cancer of the present invention comprises administering a therapeutically effective dose of the above apoptosis-inducing agent to mammals with cancer.

Examples of mammals include humans, dogs, cats, sheep, goats, cattle, horses, and pigs. "Therapeutically effective dose (for cancer)" means an amount that stops cancer cell proliferation, reduces tumor size, or causes disappearance of tumor when the agent is administered to proliferating cancer cells.

The specific dose should be appropriately increased or decreased depending on the administration route, the age and body weight of a patient, the type and malignancy of cancer, the presence or absence of metastasis or recurrence, and the like.

Examples of the route of administration include intravenous, intra-arterial, intramuscular, intraperitoneal, subcutaneous, local, intratumoral, oral, percutaneous, intrarectal, intravaginal, intranasal, and sublingual administration. Specifically, for example, for solid tumors within various organs that are easily accessible by surgical operation, the agent may be administered into such tumors or locally injected in the vicinities of such tumors using a stereotaxic needle or the like. For cancer at sites that are not easily accessible by surgical operation, such as non-solid tumors such as leukemia, brain tumor, and metastatic cancer, the agent can be administered by intravenous injection. Furthermore, the above administration methods can be appropriately selected and used depending on the type, site, and the like of cancer.

As modes of gene therapy, there exist an ex vivo method that involves collecting target cells outside the body and introducing genes into the cells and an in vivo method that involves introducing genes into bodies. The apoptosis-inducing agent of the present invention is also applied in both modes for therapy. In the case of the ex vivo method, cells derived from a patient are cultured outside the body, the above polynucleotide is introduced into the cells, and then the resultant is administered to the patient. In the case of the in vivo method, a vector having the polynucleotide introduced therein is directly administered into a patient's body (e.g., organ tissue, skin, or muscle).

Furthermore, such cancer treatment may be used together with known cancer therapeutic means including surgical operation, chemical therapy, and radiation therapy.

BEST MODE OF CARRYING OUT THE INVENTION

The present invention will be hereafter described in detail by referring to examples, but the invention is not limited by these examples Example 1

Preparation of Expression Plasmids and Collection of Cancer Tissue Samples (1) Preparation of Expression Plasmids A full-length FIR cDNA (SEQ ID NO: 2) and an FIR mutant wherein an amino acid sequence of 77 N-terminal-side amino acids (the amino acid sequence between amino acid positions 1 and 77 in the amino acid sequence of SEQ ID NO: 2) corresponding to an FIR transcriptional activity site had been deleted were cloned into pCGNM2 vector plasmids (Liu, J. et al., Cell, 104; 353-363, 2001). Thus, expression plasmids (HA-FIR and HA-FIRΔN77) were prepared for both the cDNA and the mutant.

Furthermore, pcDNA3.1-c-myc, GeneStorm™ Expression-Ready Clones (Invitrogen Co., AL) was purchased for a human c-Myc expression vector.

(2) Collection of Human Colorectal Cancer Tissue Samples

Tissues were surgically excised from 15 primary colorectal cancer patients (written informed consent had been obtained from each patient prior to surgery). The excised samples were collected within 1 hour after operative excision from tumor epithelial tissues and non-tumor epithelial tissues that were 5 to 10 cm away from the tumor. Two pathologists microscopically confirmed that all tissue samples were adenocarcinomas. All excised samples were immediately placed in liquid nitrogen and stored at −80° C. until further analysis.

Example 2

Test for the Suppression of Foreign c-myc Gene Transcription by FIR

To examine whether or not FIR has ability to suppress the transcription of a exogenous c-myc promoter, a reporter plasmid having the c-myc promoter located upstream of a chloramphenicol acetyl transferase (CAT) gene was co-transfected with HA-FIR or HA-FIRΔN77 (prepared in Example 1) into HeLa cells and then CAT expression was examined.

(1) Method (CAT Assay)

HeLa cells were cultured in Dulbecco's Modified Eagle's media (DMEM, Gibco-BRL) supplemented with 10% fetal calf serum. HA-FIR or HA-FIRΔN77 was then introduced together with the reporter plasmid having the c-myc promoter located upstream of the chloramphenicol acetyl transferase (CAT) gene into the HeLa cells by electroporation. 48 hours after gene introduction, CAT expression was examined according to descriptions in literature (Tomonaga, T. et al., J. Biol. Chem., 270: 4875-4881, 1995).

(2) Results

FIG. 1 shows the results of CAT assay. FIR significantly suppressed CAT expression. However, compared with the case of normal FIR, suppression of CAT expression was attenuated in the case of the mutant FIR from which the amino terminus had been deleted (FIG. 1).

Example 3

Test for the Suppression of Endogenous c-myc Gene Transcription by FIR

Whether or not the transcription of a c-myc gene promoter (endogenous c-myc promoter), which is originally present within cells, is suppressed by FIR was examined by immunohistochemical staining and flow cytometric analysis.

(1) Method (1-1) Immunohistochemical Staining

HeLa cells were cultured on cover glasses overnight and then transfected with plasmids (HA-FIR and HA-FIRΔN77) using Lipofectamine Plus reagent (Gibco BRL). 24 hours after the introduction of the plasmids, the cells were treated according to the description of a previous report (He, L., et al., Embo J, 19: 1034-1044, 2000).

The cells on the cover glasses were fixed with 4%-paraformaldehyde, washed with PBS, and then allowed to react with primary antibodies at room temperature for 1 hour. A mouse anti-HA monoclonal antibody (Santa Cruz Biotechnology, CA), a rabbit anti-c-Myc polyclonal antibody (Upstate Biotechnology, NY), and a mouse anti-c-Myc monoclonal antibody (Oncogene Research Products, CA) were diluted 500 fold, 1,000 fold, and 500 fold, respectively, with a blocking buffer, and then used as primary antibodies.

Subsequently, the cells were washed again with PBS and then allowed to react with secondary antibodies [rhodamine-labeled anti-mouse IgG (Roche) and fluorescein isothiocyanate (FITC)-conjugated-anti-rabbit IgG (Sigma) that had been diluted 1,000 fold and 500 fold, respectively, with the above blocking buffer]. The DNAs of cell nuclei were stained with diamidinophenylindole (DAPI, 1 μg/ml) and then observed with an immunofluorescent microscope (Leica QFISH; Leica Microsystems, Tokyo, Japan).

(1-2) Flow Cytometric Analysis

The cells were subjected to two-color FACScan analysis (He, L., et al., Embo J, 19: 1034-1044, 2000) to quantify the suppression of c-Myc expression by FIR. Specifically, 22 hours after transfection, the cells were trypsinized, washed with PBS, and then fixed with ethanol at −20° C. for at least 2 hours. The cells were then washed twice with cold PBS and then allowed to react with mouse anti-HA antibody and rabbit anti-c-Myc antibody as primary antibodies. After washing with PBS, the cells were allowed to react with secondary antibodies [FITC-conjugated-anti-rabbit IgG (Sigma) and R-PE-conjugated-anti-mouse IgG (PharMingen), each of which had been diluted 200 fold].

10,000 cells of each sample were analyzed by flow cytometry with the setting of c-Myc-FITC into FL1 intensity and HA-PE into FL2 intensity. Transfected cells (PE-positive cells) were plotted on the X axis and FITC-positive cells (c-Myc-expressing cells) were plotted on the Y axis.

(2) Results

Figure 2:
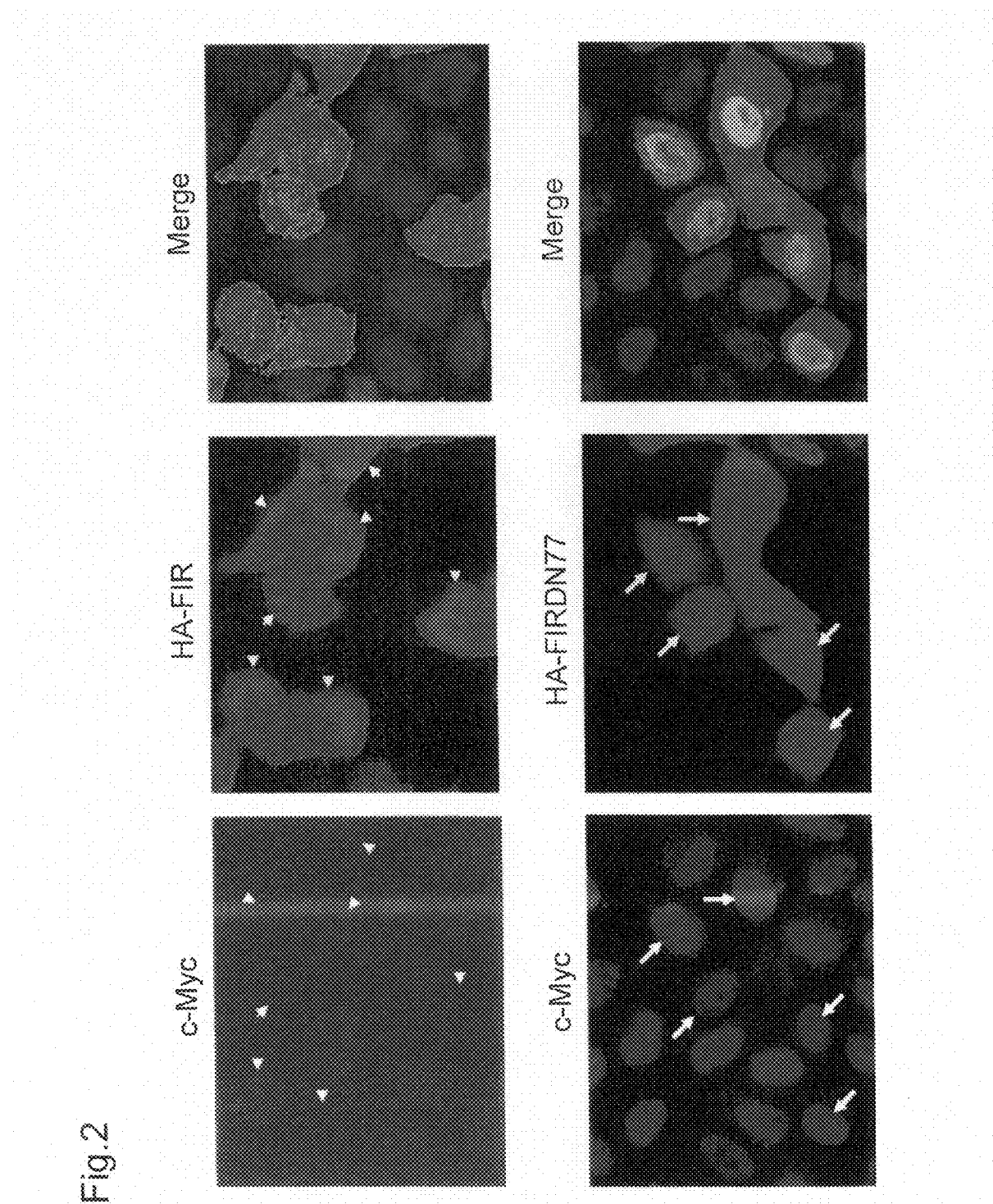
FIG. 2 shows fluorescence microscope photographs showing c-Myc protein expression in HeLa cells wherein a full-length FIR gene (HA-FIR) or a mutant deficient in FIR(HA-FIRΔN77) was introduced, as visualized by immunohistochemical staining.

FIG. 2 shows endogenous c-Myc expression visualized by immunohistochemical staining after transfection of HeLa cells with HA-FIR and HA-FIRΔN77.

HA-FIR-expressing cells showed significantly suppressed c-Myc expression levels (FIG. 2, upper panels, indicated with "▲"). In contrast, HA-FIRΔN77-expressing cells showed attenuated suppression activity thereof (FIG. 2, lower panels, indicated with arrows).

Figure 3:
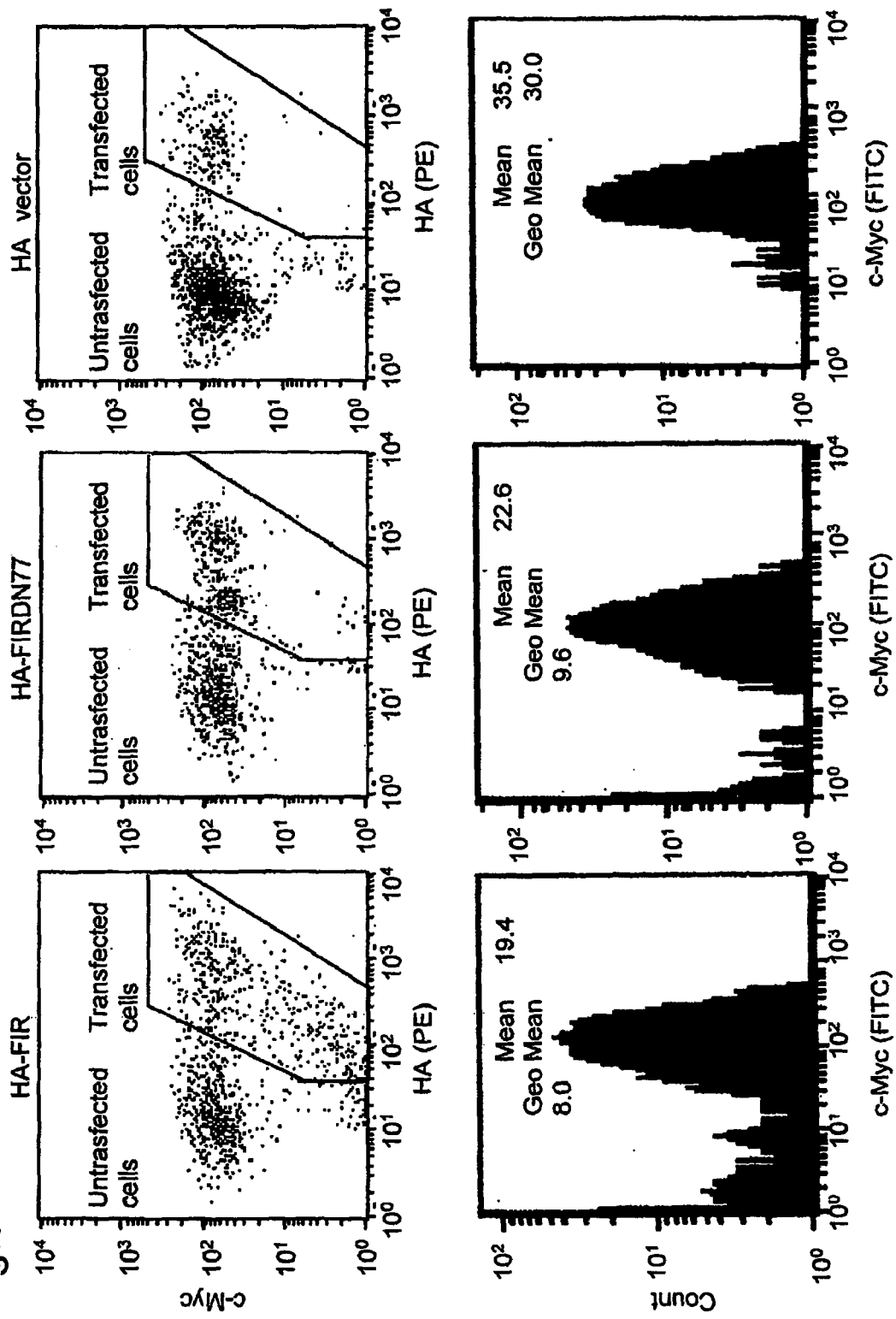
FIG. 3 shows c-Myc protein expression in HeLa cells wherein the full-length FIR gene (HA-FIR) or the mutant deficient in FIR (HA-FIRΔN77) was introduced, as quantified by flow cytometric analysis (two-color FACScan analysis).

FIG. 3 shows endogenous c-Myc expression quantified by flow cytometric analysis (two-color FACScan analysis) after transfection of HeLa cells with HA-FIR and HA-FIRΔN77. Whereas HA-FIR suppressed c-Myc expression (FIG. 3, upper left panel), HA-FIRΔN77 did not have such action (FIG. 3, upper central panel) and c-Myc expression was not suppressed in the case of HA vector alone (FIG. 3, upper right panel).

Within the HA-FIR-positive population, the c-Myc levels were significantly bimodal in the gated region (FIG. 3, upper left panel) and c-Myc levels in HA-FIR-transfected cells sharply decreased. In the HA-FIRΔN77- or HA-tag-transfected cells, c-Myc expression levels were uniformly indistinguishable between transfected cells and untransfected cells (FIG. 3, upper central and right panels).

Lower panels show histograms of c-Myc expression in the gated regions marked in the upper panels. Mean values (Geomean) of c-Myc in the gated regions were: 19.4 (8.0) in the case of HA-FIR, 22.6 (9.6) in the case of HA-FIRΔN77, and 35.5 (30.0) in the case of HA-vacant vector.

As described above, it was confirmed that FIR suppresses endogenous c-Myc expression and that an FIR amino-terminal domain is essential for such expression.

Example 4

Cell Death (Apoptosis) Induction by FIR

FIR suppresses endogenous c-myc expression. Whether or not apoptosis can be induced by high-level expression of FIR is examined using a full-length FIR and a mutant FIR wherein an amino acid sequence consisting of 76 N-terminal amino acids had been deleted.

(1) Method (TUNEL Assay)

150 fmol of HA-FIR or HA-FIRΔN77 and vacant vector plasmids were transfected to HeLa cells in 6-well plates. 60 hours later, apoptosis induction was examined. Apoptotic cells were detected by TUNEL assay according to the manufacturer's instructions (Apoptosis Detection System, Fluorescein. Promega, Wis., U.S.A.). Specifically, HeLa cells were cultured on cover glasses and then fixed on ice with 4%-paraformaldehyde for 10 minutes. After washing with PBS, the cells were permeabilized with a 0.5% triton-X-100 PBS solution for 5 minutes. After washing twice with PBS, apoptotic cells were visualized through detection of intranucleosomal fragmentation of DNA using in situ nick-end labeling with terminal deoxytransferase (TdT) containing FITC-labeled-dUTP (MEBSTAIN Apoptosis Kit: Medical & Biological Laboratories, JAPAN).

HeLa cells were treated with 1 unit/ml DNase I (Gen-Hunter Corporation, Nashville, Tenn.) and then used as positive control cells. DNA was stained with DAPI III Counterstain (Vysis, Abbott Park, Ill.) and then the cells were observed with a fluorescence microscope (Leica QFISH; Leica Microsystems, Tokyo, Japan).

Upon two-color FACScan analysis, cells were trypsinized and then fixed with ethanol at −20° C. for at least 2 hours. After washing with PBS twice, the cells were incubated in 50 μl of TdT buffer containing FITC-labeled-dUTP. Subsequently, the cells were resuspended in a 0.5 ml of propidium iodide (PI) solution (freshly diluted with PBS to 5 μg/ml) containing 250 μg of DNase-free RNase A. 10,000 cells per sample were analyzed with the setting of FITC into FL1 intensity and PI into FL2 intensity. PI-positive cells were plotted on the X axis and FITC-positive cells (apoptosis-positive cells) were plotted on the Y axis.

(2) Results

Figure 4:
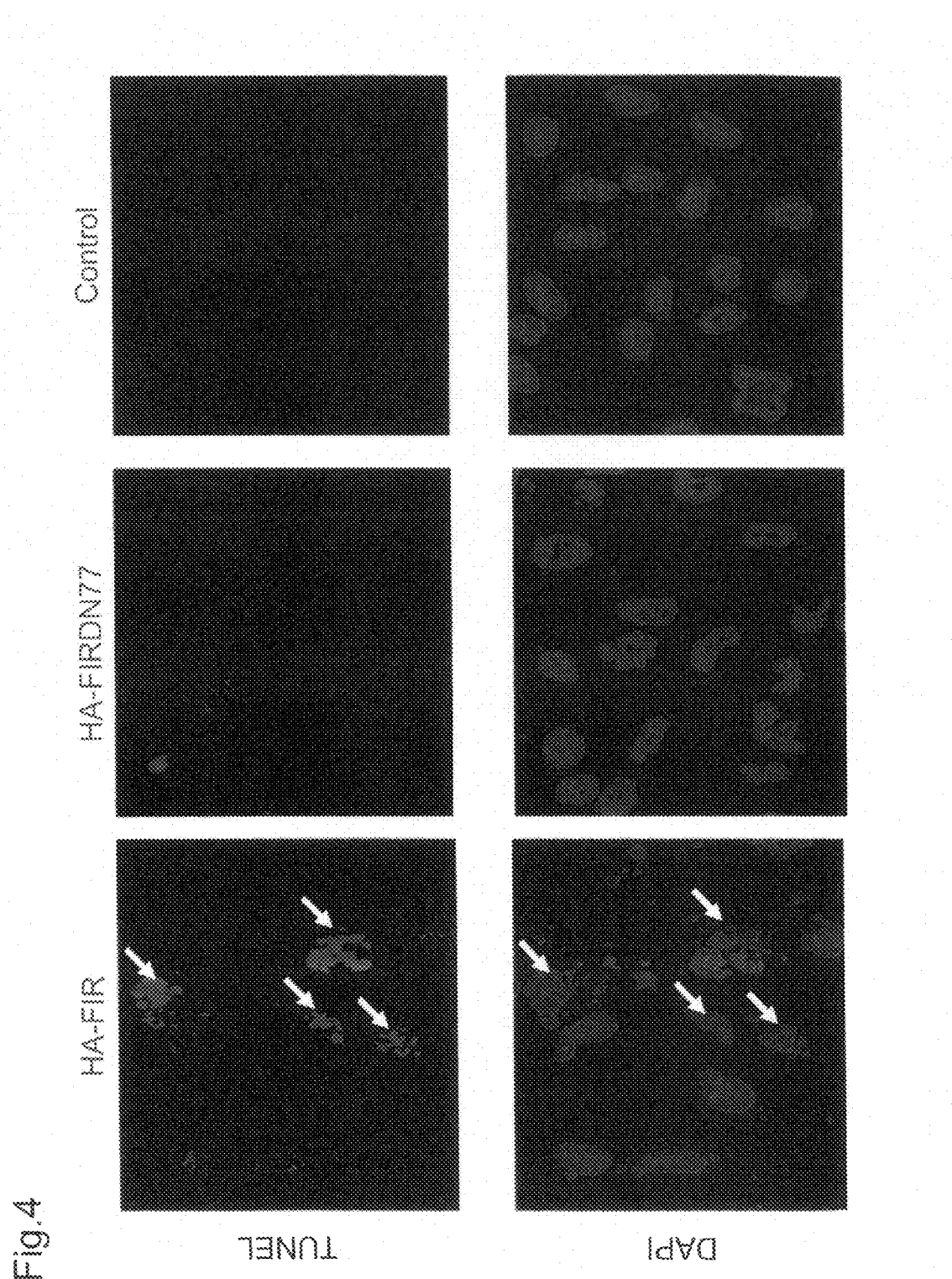
FIG. 4 shows fluorescence microscope photographs showing the results of examining apoptosis induction in HeLa cells wherein the full-length FIR gene (HA-FIR) or the mutant deficient in FIR (HA-FIRΔN77) was introduced.

HA-FIR induced apoptosis accompanied by DNA fragmentation (FIG. 4, upper left panel, indicated with arrows). In contrast, in the cells transfected with HA-FIRΔN77 or the control vector (HA-vacant vector), almost no apoptosis was induced (FIG. 4, upper central and right panels).

Figure 5:
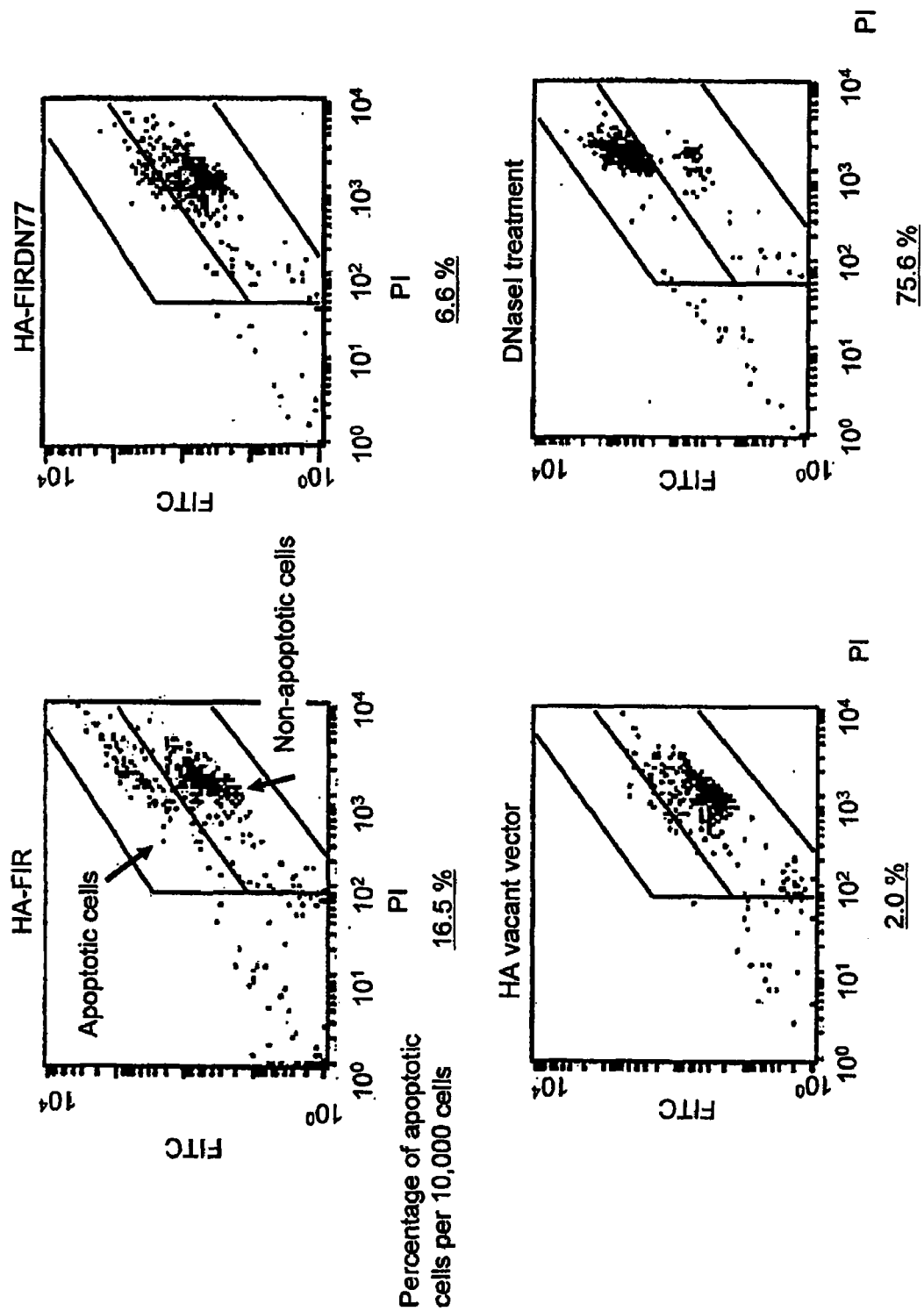
FIG. 5 shows apoptotic cells in HeLa cells wherein the full-length FIR gene (HA-FIR) or the mutant deficient in FIR (HA-FIRΔN77) was introduced, as quantified by flow cytometric analysis (two-color FACScan analysis).

FIG. 5 shows apoptotic cells quantified by two-color analysis. Apoptotic cells observed in the upper-gated regions in each panel are shown in the figure. The percentage of apoptotic cells per 10,000 cells in the case of HA-FIR was 16.5%, 6.6% in the case of HA-FIRΔN77, 2.0% in the case of HA-vacant vector, and 75.6% in the case of DNaseI-treated cells (positive control).

Example 5

Cell Death (Apoptosis) Induction by Coexpression of FIR and c-Myc (1) Method (TUNEL Assay)

600 ng of pcDNA3.1-FIR was transfected into semi-confluent Hela cells inoculated on 6-well plates with or without 60 ng of a c-Myc expression plasmid (pcDNA3.1-c-myc). Analysis was carried out in a manner similar to the above by TUNEL assay.

(2) Results

Figure 6:
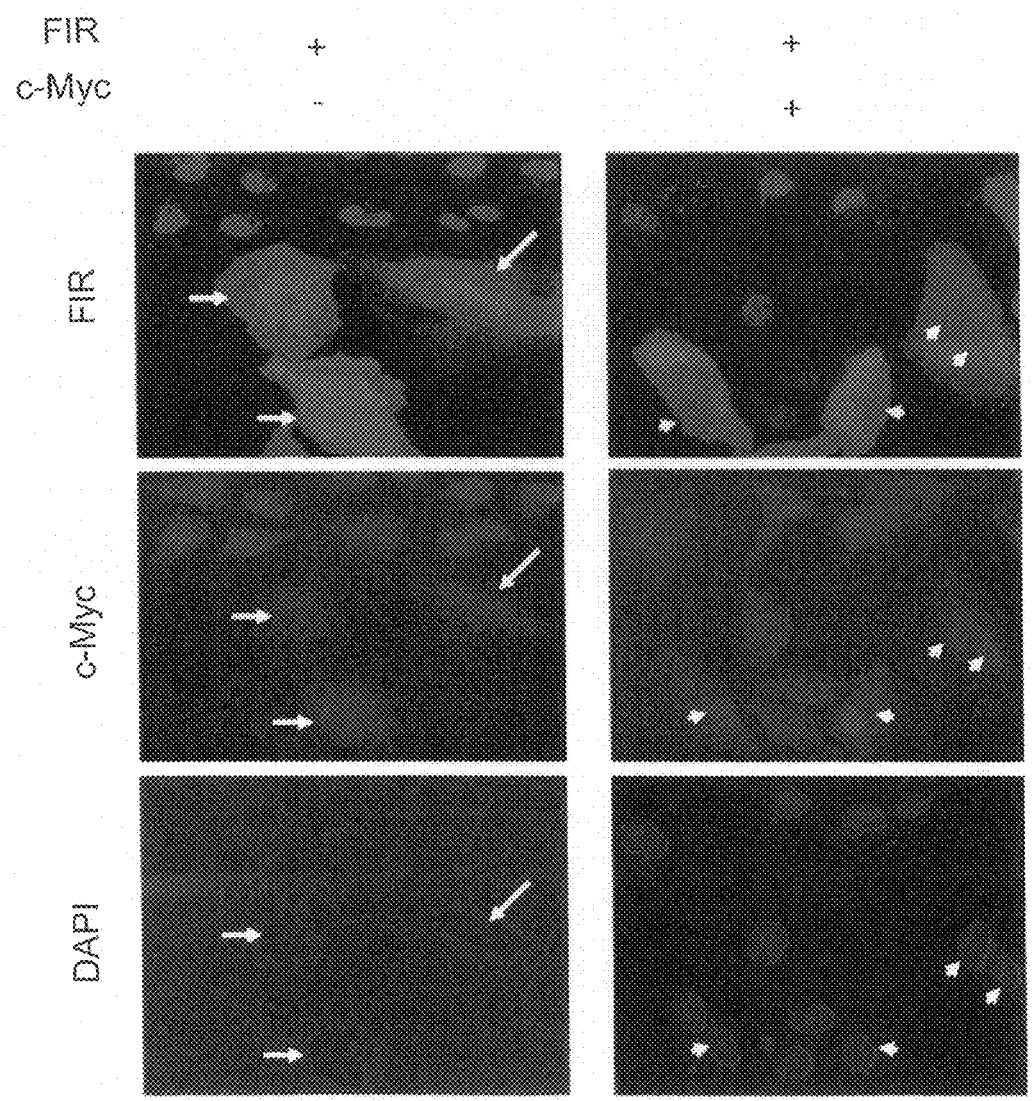
FIG. 6 shows fluorescence microscope photographs showing FIR protein expression with or without c-Myc protein expression in HeLa cells wherein the FIR gene alone or both the FIR gene and the c-myc gene were introduced, as visualized by immunohistochemical staining.

Whereas c-Myc expression was significantly elevated in the case of co-transfection with the c-myc plasmid and FIR plasmid (FIG. 6, middle right panel), c-Myc expression was significantly suppressed in the case of transfection with FIR alone (FIG. 6, middle left panel). Regarding nuclear fluorescence images (DAPI staining), compared with c-myc-coexpressing cells (FIG. 6, bottom right panel), swollen and degraded nuclei were confirmed in cells that expressed FIR alone (FIG. 6, bottom left panel).

Figure 7:
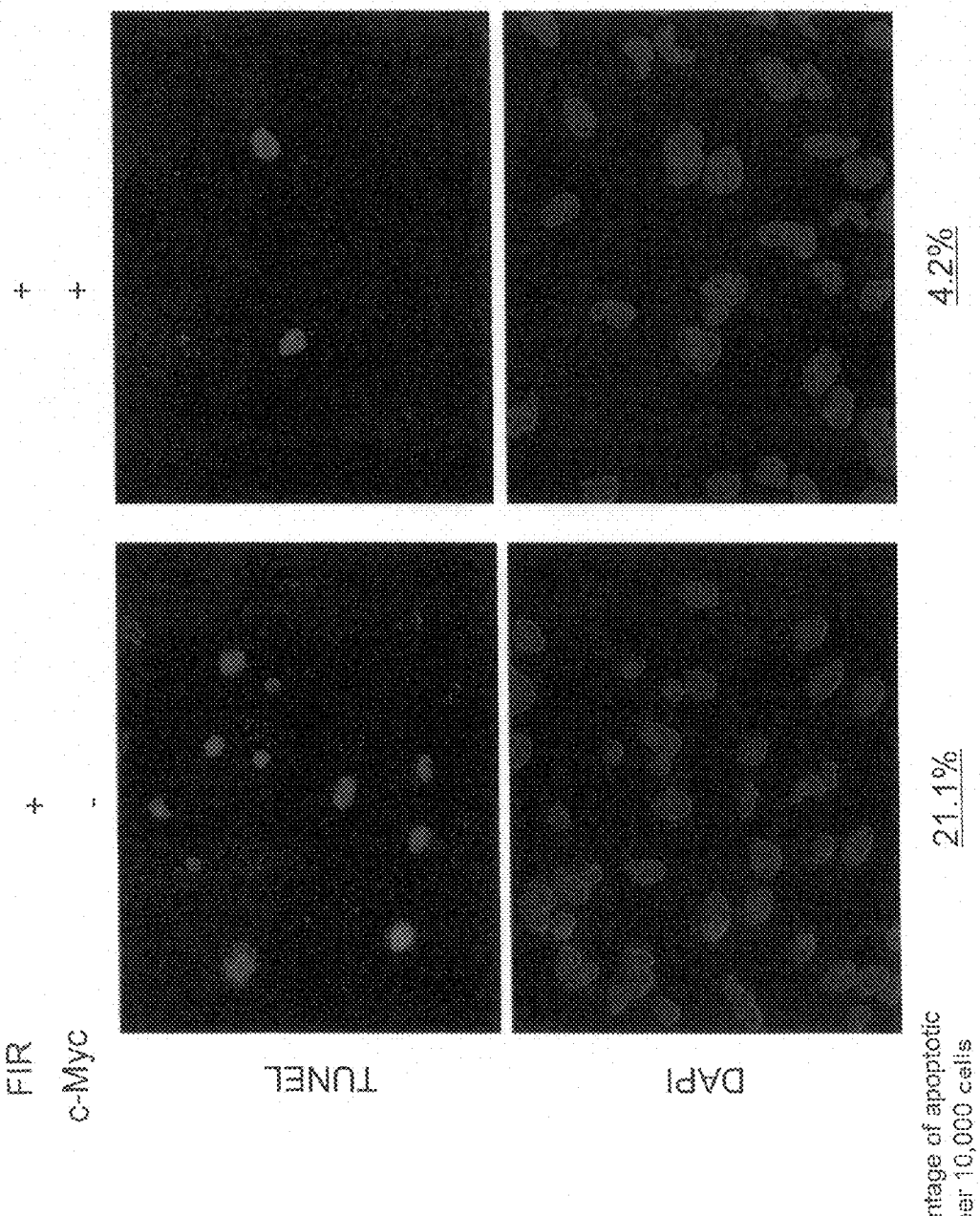
FIG. 7 shows fluorescence microscope photographs showing the results of examining apoptosis induction in HeLa cells wherein the FIR gene alone or both the FIR gene and the c-myc gene were introduced.

Regarding the number of apoptotic cells, whereas the percentage of apoptotic cells was 21.1% in the case of FIR alone, the percentage of the same drastically decreased to as low as 4.2% in the case of cotransfection with the c-myc expression plasmids (FIG. 7).

Furthermore, Table 1 shows the result of examining the number of apoptotic cells when the c-myc plasmid and the FIR plasmid were cotransfected into cells at various ratios. These results suggest that apoptosis induction by FIR is caused by c-Myc suppression.

TABLE 1

| Introduced plasmid | | | | | | | |
|---|---|---|---|---|---|---|---|
| pcDNA3.1-FIR (ng) | 600 | 600 | 600 | 600 | 600 | 600 | 0 |
| pcDNA3.1-c-myc (ng) | 0 | 0 | 10 | 20 | 50 | 60 | 60 |
| pcDNA3.1 vector (ng) | 0 | 60 | 50 | 40 | 10 | 0 | 0 |
| Percentage (%) of apoptotic cells per 10,000 cells | 17.3 | 21.1 | 4.2 | 5.6 | 6.7 | 7.0 | 7.5 |

Example 6

Analysis of FIR Protein and FIR mRNA in Tumor and Normal Tissues (1) Method (1-1) Protein Extraction and Immunoblotting Total protein lysates were prepared from the above matched samples as follows. Frozen tissue samples were dissolved in lysis buffers [7 M urea, 2 M thiourea, 2% 3-[3-Cholamidopropyl)dimethylammonio-] 1-propanesulfate (CHAPS), 0.1 M dithiothreitol (DTT), 2% IPG buffer (Amersham Pharmacia Biotech, Buckinghamshire, UK), and 40 mM Tris] using a Polytron homogenizer (Kinematica, Switzerland), followed by centrifugation (100,000×g) at 4° C. for 1 hour. The amounts of protein in the supernatants were measured by protein assay (Bio-Rad, Hercules, Calif.). The proteins were subjected to electrophoresis on 8% acrylamide gel and then transferred to polyvinylidene fluoride membranes (Millpore, Bedford, Mass.) in a tank transfer apparatus (Bio-Rad, Hercules, Calif.). The membranes were blocked with a 5% skim milk PBS solution for 1 hour. A rabbit anti-FIR polyclonal antibody (that had been prepared by simultaneous immunization with two synthetic peptides, consisting of amino acid residues 30-45 and amino acid residues 528-542 of SEQ ID NO: 1, in order to enhance the possibility of antibody production) was diluted 1000-fold and 500-fold with a blocking buffer. A goat anti-β-actin polyclonal antibody (Santa Cruz, Santa Cruz, Calif.) was diluted 1000-fold and 500-fold with a blocking buffer. These diluted antibodies were used as primary antibodies. A goat anti-rabbit IgG horseradish peroxidase conjugate (HRP) (Jackson, West Grove, Pa.) diluted 3000-fold and rabbit anti-goat IgG HRP (Cappel, West Chester, Pa.) diluted 500-fold were used as secondary antibodies. Antigens on the membranes were detected using an ECLTM detection reagent (Amersham Pharmacia Biotech). Immunoblotting was carried out using a β-actin antibody as a loading control. The intensity of each band was measured by NIH Image.

(1-2) RT-PCR and Real-Time Quantitative PCR

Total RNA and genomic DNA were extracted from tumor and non-tumor epithelial tissues with an RNeasy™ Mini Kit and a DN Easy™ Tissues Kit (Qiagen). cDNA was synthesized from total RNA using a 1st strand cDNA Synthesis Kit for RT-PCR (Roche, Mannheim, Germany). FIR cDNA was amplified by RT-PCR using the cDNA as a template and primers (forward: 5'-GGCCCCATCAAGAGCATC-3' (SEQ ID NO: 3) and reverse: 5'-GGGGCTGGGCCAGGGTCAG-3') (SEQ ID NO: 4)). As a control, GAPDH cDNA was amplified.

FIR cDNA was subjected to real-time quantitative PCR using a Light Cycler™ instrument (Roche, Mannheim, Germany) in 20 µl of a reaction mixture consisting of a master mixture [LightCycler™-FastStart DNA Master SYBR Green I containing FastStart Taq DNA polymerase, a dNTP mixture, a buffer (LightCycler™ DNA Master hybridization probes, Roche), 3.0 mM $MgCl_2$, 0.5 µM each of sense and antisense primers, and 1 µl of a template cDNA in LightCycler™ capillary]. LightCycler™ software version 3.3 (Roche) was used for quantitative RT-PCR analysis. Optimization of the primers and LightCycler™ conditions were conducted at Nihon Gene Research Laboratories, Inc.

Primers for amplifying FIR cDNA by real-time quantitative PCR are as follows (PCR product size is 275 bp).

```
Forward: 5'-GCACCTGGAGTCATCACA-3'    (SEQ ID NO: 5)

Reverse: 5'-CGCAGAACCATCACTGTAG-3'   (SEQ ID NO: 6)
```

PCR products obtained by the use of these primers were purified using a Qiagen PCR product purification kit, so as to determine quantification curves for the Light Cycler™.

FIR genomic DNA was also quantified by real-time quantitative PCR using the following primers.

```
Forward: 5'-GGAGTCTACAGTGATGGTTC-3'  (SEQ ID NO: 7)

Reverse: 5'-TCCTGGTCGTACACTTCA-3'    (SEQ ID NO: 8)
```

Primers for human c-myc cDNA and human β-actin cDNA are as follows.

```
(for c-myc)
Forward: 5'-GCCTCAGAGTGCATCGAC-3'    (SEQ ID NO: 9)

Reverse: 5'-TCCACAGAAACAACATCG-3'    (SEQ ID NO: 10)

(for β-actin)
Forward: 5'-TGGAGAAAATCTGGCACCAC-3'  (SEQ ID NO: 11)

Reverse: 5'-AATGGTGATGACCTGGCCGT-3'  (SEQ ID NO: 12)
```

(2) Result

Figure 8:
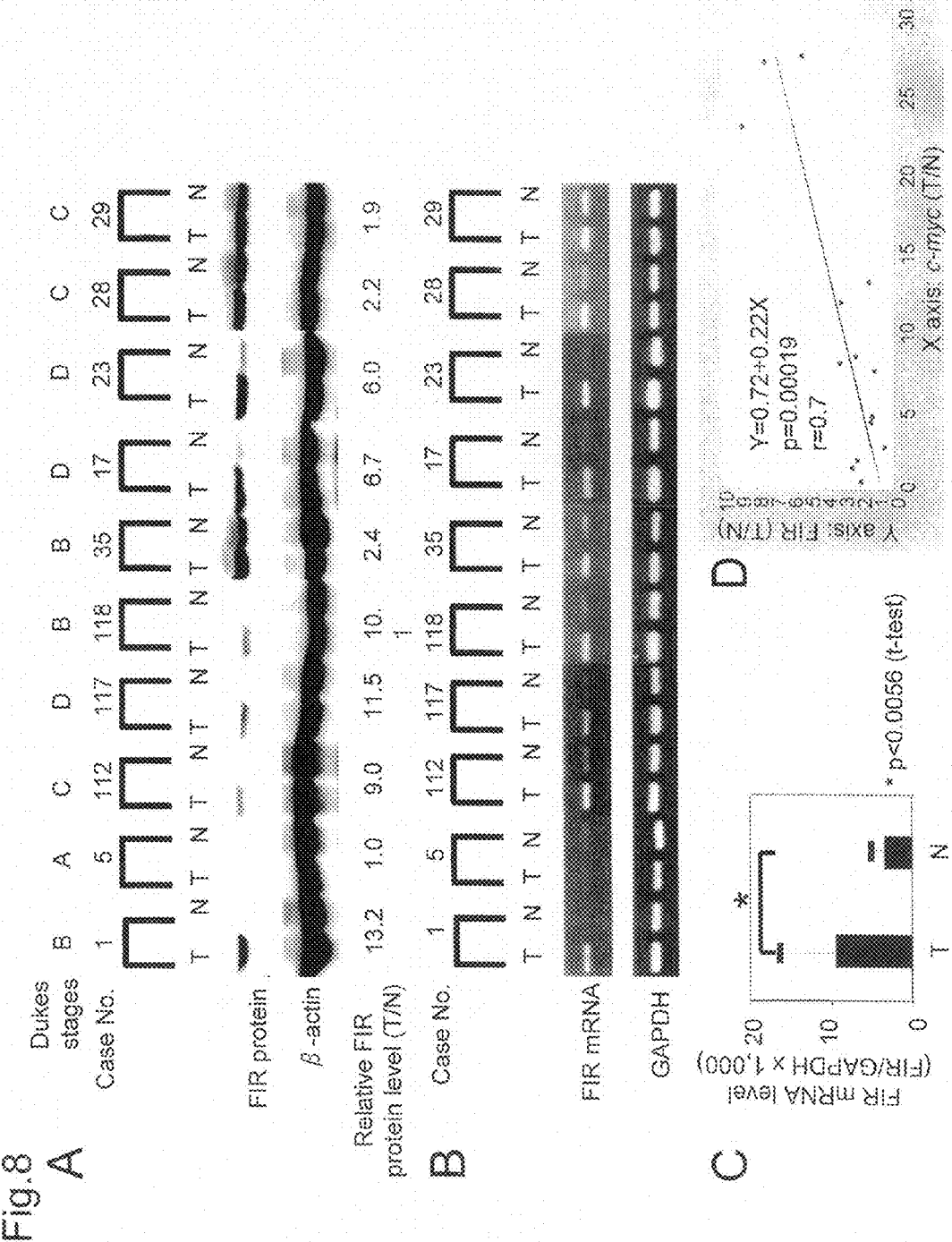
FIG. 8A shows FIR protein levels in tumor tissues (T) and non-tumor tissues (N) in the large intestine as analyzed by immunoblotting.
FIG. 8B shows the results of RT-PCR carried out for the total RNAs in tumor tissues (T) and non-tumor tissues (N) in the large intestine.
FIG. 8C shows the histogram of FIR mRNA expression levels in tumor tissues (T) and non-tumor tissues (N) in the large intestine as detected by real-time quantitative PCR.
FIG. 8D shows the correlation between the rate of FIR mRNA expression levels in tumor tissues (T)/the same in non-tumor tissues (N) and the rate of c-myc mRNA expression levels in (T)/(N) in the large intestine.

FIG. 8A shows the results of immunoblotting. The intensity of each band was measured by NIH Image. Relative mean values of FIR protein levels between (T) and (N) compared with β-actin were (the bottom of the figure) measured. Dukes stages are listed at the top of FIG. 8. Surprisingly FIR levels increased in most colorectal cancer tissues compared with corresponding non-tumor epithelia (FIG. 8A).

FIG. 8B shows the results of RT-PCR carried out for total RNA prepared from matched samples of (T) and (N). FIR mRNA levels in (T) were higher than FIR mRNA levels in (N) except for a single case (case No. 5). A GAPDH mRNA level is also shown as an internal control level.

FIG. 8C shows the histogram of FIR mRNA expression levels in (T) and (N) as detected by real-time quantitative PCR. FIR mRNA levels in (T) were significantly higher than FIR mRNA levels in (N) ($p<0.0056$ for t-test; $p<0.0008$ for Wilcoxon test).

The expression ratio ((T)/(N)) of FIR was significantly correlated with that of c-myc mRNA in each colorectal cancer tissue (FIG. 8D). The mean FIR expression level was significantly correlated with the mean c-myc expression level, as shown in Y=0.72+0.22X (Y: FIR expression ratio (T/N) and X: c-myc expression ratio (T/N)). The correlation coefficient was 0.70 and the p-value was 0.00019.

Based on these results, it can be considered that deregurations of c-Myc in colorectal cancer is not due to downregulation of FIR, but is likely due to damaged FIR functions. Conversely, it is thought that FIR is upregulated in colorectal cancer wherein FIR correlates with increased c-Myc.

Example 7

Detection and Analysis of FIR Amino Terminal Mutation (1) Method

An FIR amino terminal domain was amplified by PCR using the following primers.

```
Forward:
5'-AGACAGCGGAAGGAGCAAGAGTGG-3'   (SEQ ID NO: 13)

Reverse:
5'-CTGTGCAGCTTCGGGGACCTCATA-3'   (SEQ ID NO: 14)
```

The PCR product of the FIR amino terminal domain (NTD) was loaded on 1% agarose gel and then purified using a Gel Extraction Kit™ (Qiagen) before cloning to a pGEM™-T Easy vector system (Promega, Wis.), followed by DNA sequencing. A direct DNA sequence was confirmed by the use of at least 4 different primers (two from the forward direction and two from the reverse direction). When mutations were detected, DNA sequencing was carried out at least 8 times in total from both forward and reverse directions. Furthermore, when mutations were present in the NTD of FIR cloned into pGEM™-T Easy vector, RT-PCR product was directly sequenced so that its accuracy was confirmed.

(2) Results

When the full-length FIR cDNA was isolated from colorectal cancer tissues and then sequenced, it was surprisingly confirmed that in several cases the FIR amino terminus (amino acid positions 1 to 156) contained at least one mutation.

Figure 9:
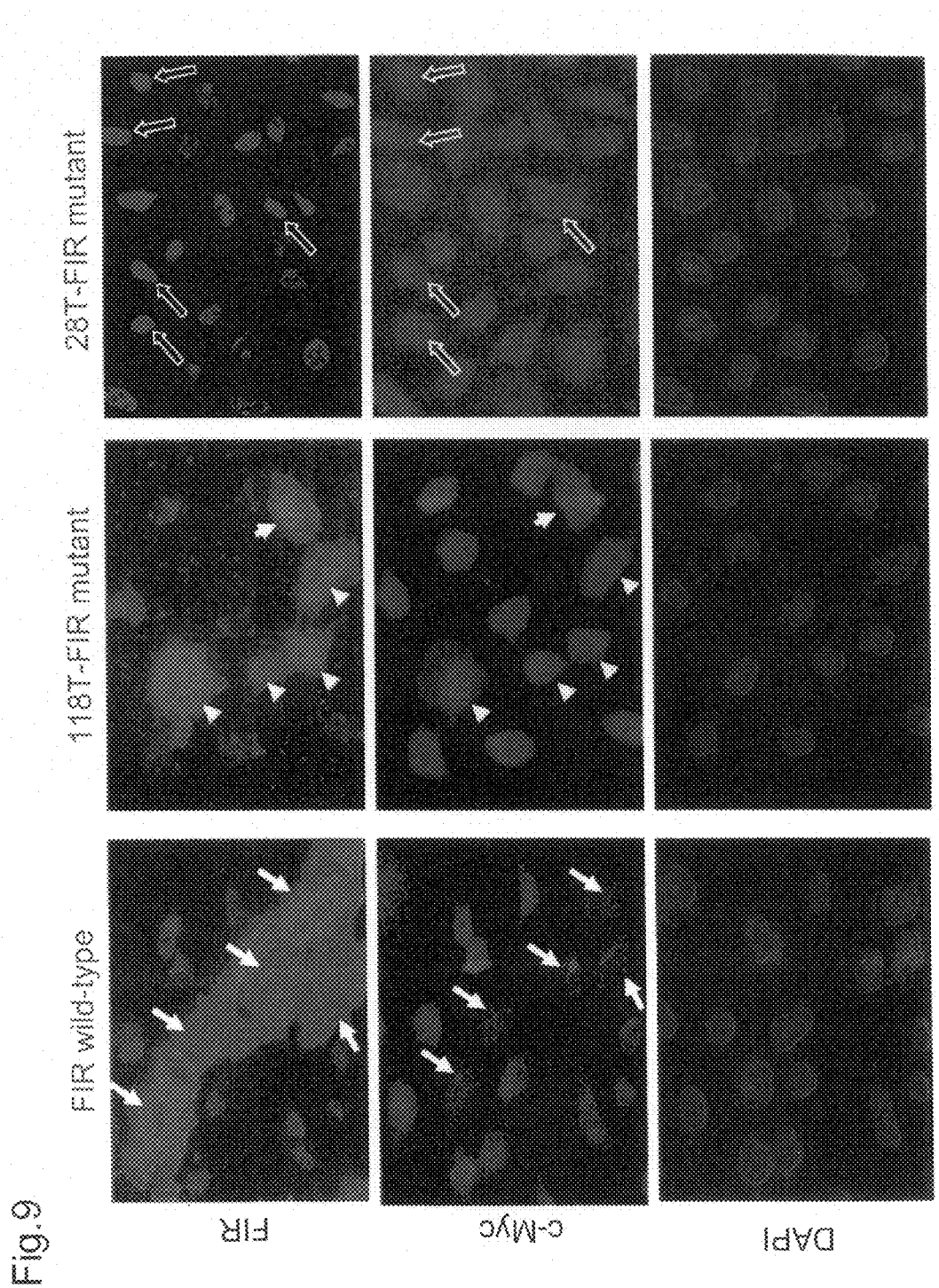
FIG. 9 shows fluorescence microscope photographs showing c-Myc protein expression in HeLa cells wherein the full-length FIR gene (FIR wild type) was introduced and in HeLa cells wherein colorectal cancer tissue-derived FIR mutants (118T-FIR mutant and 28T-FIR mutant) were introduced as visualized by immunohistochemical staining.
Figure 10:
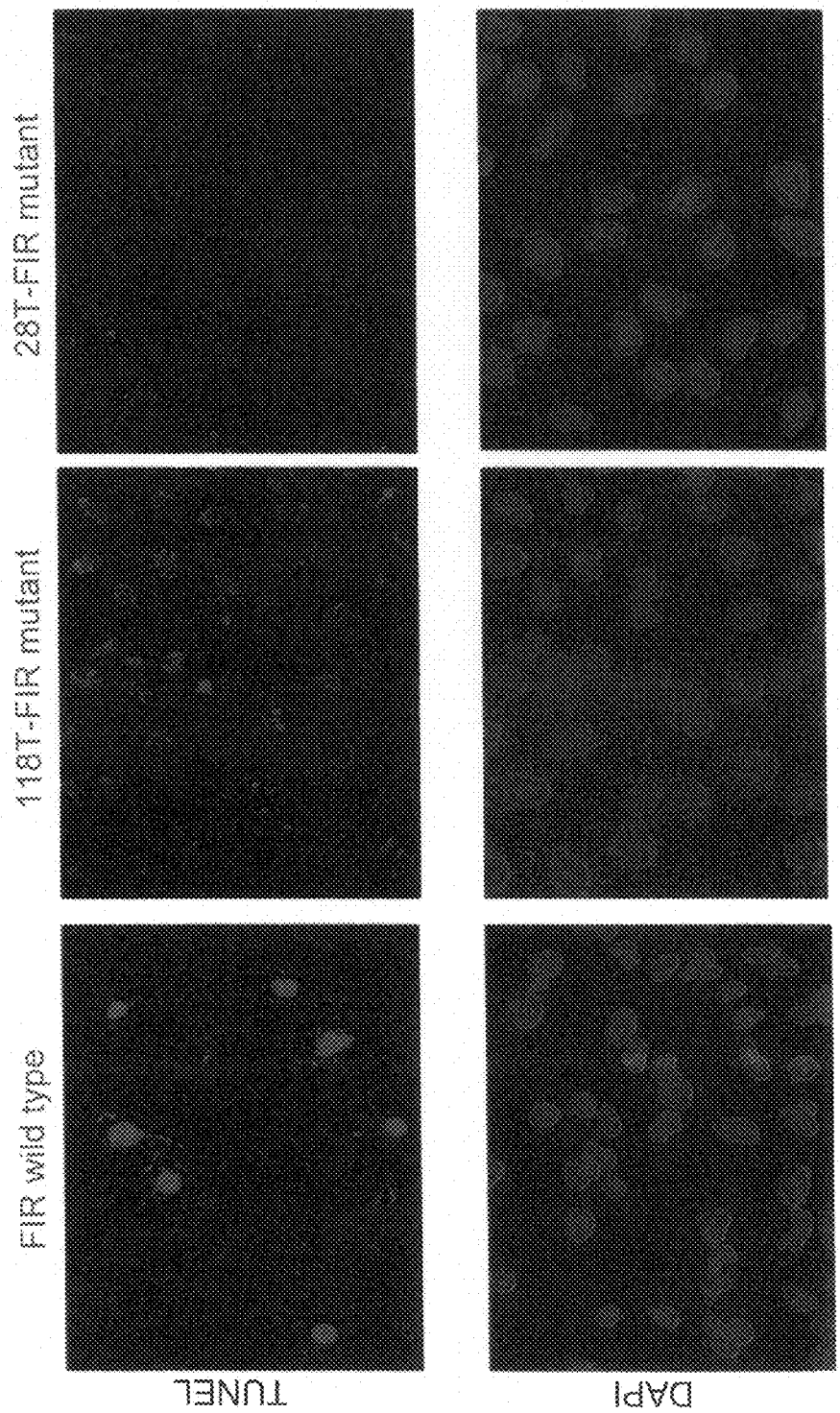
FIG. 10 shows fluorescence microscope photographs showing the results of examining apoptosis induction in HeLa cells wherein the full-length FIR gene (FIR wild type) was introduced and HeLa cells wherein the colorectal cancer tissue-derived FIR mutants (118T-FIR mutant and 28T-FIR mutant) were introduced.

The full-length FIR cDNA (HA-FIR) and the cDNA clones of 2 cases of the above mutants, a 28T-FIR mutant (having G deletion (GGG to GG_) at codon 55 and stops at codon 59) and a 118T-FIR mutant (having 4 point mutations, of which the mutation at codon 90 is due to amino acid substitution (His (CGC) to Arg (CAC)), were each cloned into a pcDNA3.1 plasmid. The resultant plasmids were then introduced into Hela cells. FIGS. 9 and 10 show the results of examining c-Myc suppression activity and apoptosis induction.

The expression of an FIR-wild type, that of the 118T-FIR mutant, and that of the 28T-FIR mutant were stained red (FIG. 9, top panels). Whereas the FIR-wild type and the 118T-FIR mutant were expressed in all cells, the 28T-FIR mutant was localized only in the nuclei. c-Myc was stained green (FIG. 9, middle panels) and DNA was counterstained with DAPI III (FIG. 9, bottom panels). In both the 118T-FIR mutant and the 28T-FIR mutant, c-Myc suppression activity was decreased compared with that of the FIR-wild type.

Furthermore, apoptosis induction deteriorated in both the 118T-FIR mutant and the 28T-FIR mutant (FIG. 10).

As described above, the FIR amino terminal domain mutated in human colorectal cancer tissues. It was suggested that such mutation causes deterioration in FIR functions to suppress c-Myc and to induce apoptosis.

Example 8

Infection Test with FIR Adenovirus Vector

Figure 11:
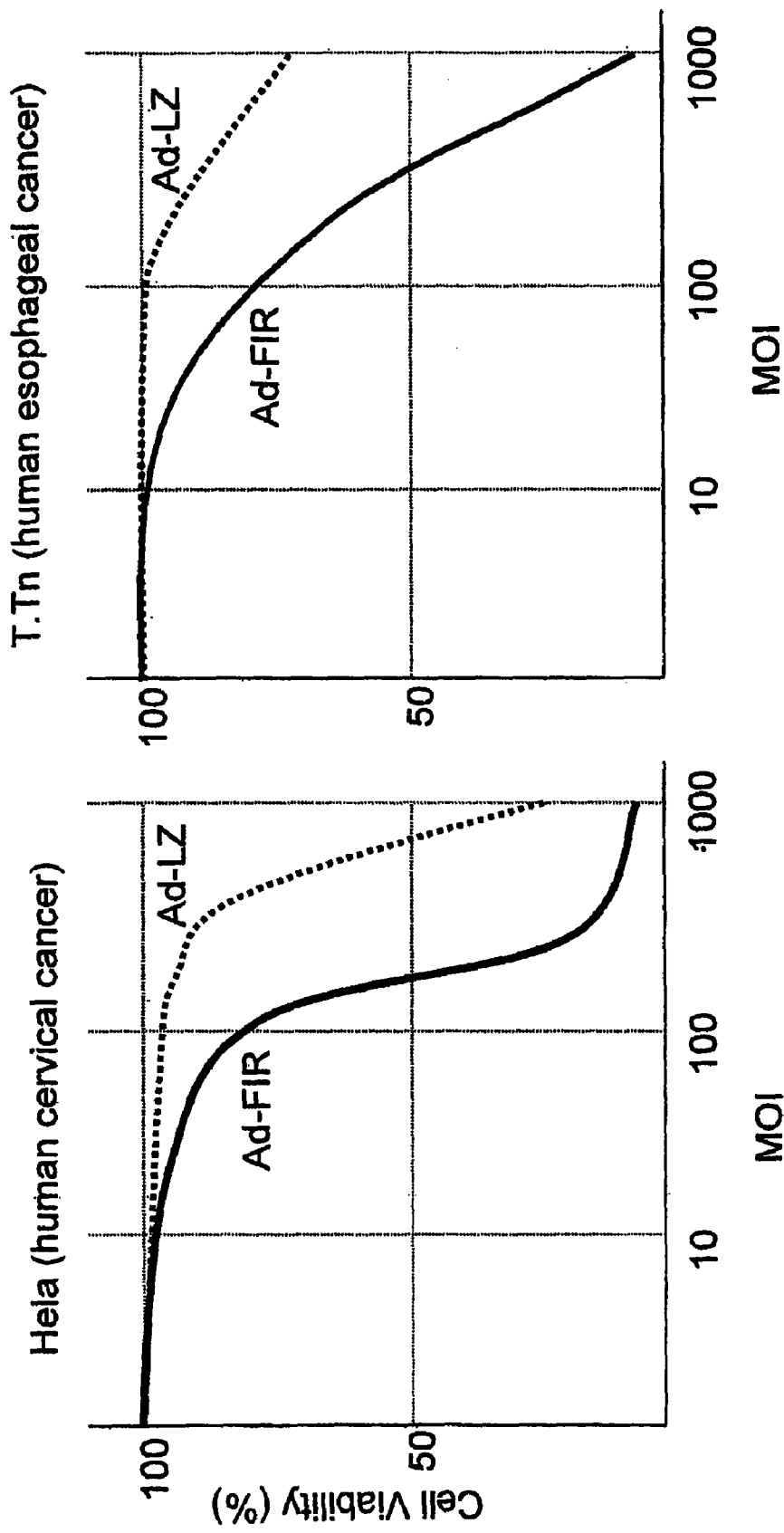
FIG. 11 shows graphs of the cell viability (%) of cervical cancer (HeLa) cells and the cell viability (%) of esophageal cancer (T.Tn) cells as measured by MTT assay.

FIR adenovirus vectors ($1.01 \times 10^{10}$ ifu/ml) were prepared. Each cell line of cervical cancer (HeLa) and esophageal cancer (T.Tn) was infected with the vectors. Suppression of cell proliferation was quantified by MTT assay. A β-galactosidase gene was expressed as a control and compared with the case of the FIR adenovirus vector. When the MOI of the FIR adenovirus vector that had reduced the number of cells by 50% was measured, it was found to be 191.4 (532.8) in the case of HeLa cells and 615.1 (1410.6) in the case of T.Tn cells (the numbers in parentheses are the MOI figures for the β-galactosidase gene). FIG. 11 shows graphs of the cell viability (%) of HeLa cells and the cell viability (%) of T.Tn cells as measured by MTT assay. The anti-tumor effect of the FIR adenovirus vector was confirmed in these cancer cells expressing c-Myc at high levels.

FIG. 12 shows FIR protein expression within nuclei and the same in the cytoplasm of each cancer cell line of colorectal cancer (SW480, DLD1), cervical cancer (HeLa), and esophageal cancer (T.Tn) after infection with the FIR adenovirus vector, as analyzed by immunoblotting. Differences in infection efficiency of the FIR adenovirus vector were observed in colorectal cancer (SW480, DLD1) cells and esophageal cancer (T.Tn) cells. In the case of T.Tn cells, although the infection efficiency of the FIR adenovirus vector was low (low protein expression level), the cell-killing effect was high.

All publications, patents, and patent applications cited herein are incorporated herein by reference in their entirety.

INDUSTRIAL APPLICABILITY

The present invention provides a novel means for stably and surely inducing cell apoptosis using the c-myc gene as a target, thereby opening a new path for cancer therapy.

The invention claimed is:

1. A method for inducing apoptosis, which is a method for inducing apoptosis in a cell that proliferates due to the expression of a c-myc gene and which comprises a step of introducing a protein consisting of the amino acid sequence represented by SEQ ID NO: 2 in the sequence listing; a protein consisting of an amino acid sequence derived from the amino acid sequence represented by SEQ ID NO: 2 in the sequence listing by deletion, substitution, or addition of 1 or several amino acids and having apoptosis-inducing activity; or a partial peptide thereof into the in vitro cell.

2. The method according to claim 1, wherein the cell is a cancer cell.

* * * * *